United States Patent [19]
Ginestet

[11] Patent Number: 5,880,473
[45] Date of Patent: Mar. 9, 1999

[54] MULTIFLUOR-FLUORESCENCE IN-SITU HYBRIDIZATION (M-FISH) IMAGING TECHNIQUES USING MULTIPLE MULTIBAND FILTERS WITH IMAGE REGISTRATION

[75] Inventor: Jacques Ginestet, Los Gatos, Calif.

[73] Assignee: Applied Imaging, Inc., Santa Clara, Calif.

[21] Appl. No.: 901,543

[22] Filed: Jul. 28, 1997

Related U.S. Application Data

[60] Provisional application No. 60/029,314, filed Oct. 25, 1996.

[51] Int. Cl.$^6$ .................................................. G01N 21/64
[52] U.S. Cl. ..................................... 250/458.1; 250/461.2
[58] Field of Search .......................... 250/458.1, 461.1, 250/462.1; 359/382

[56] References Cited

U.S. PATENT DOCUMENTS

| | | |
|---|---|---|
| 4,786,813 | 11/1988 | Svanberg et al. . |
| 4,833,332 | 5/1989 | Robertson, Jr. et al. ............ 250/458.1 |
| 5,127,730 | 7/1992 | Brelje et al. . |
| 5,332,905 | 7/1994 | Brooker et al. . |
| 5,371,624 | 12/1994 | Nagano et al. . |
| 5,780,857 | 7/1998 | Harju et al. ........................... 250/458.1 |
| 5,793,049 | 8/1998 | Ballard ................................. 250/458.1 |

FOREIGN PATENT DOCUMENTS 0 510 329 A2   10/1992   European Pat. Off. .

OTHER PUBLICATIONS

Axelrod, D. "total Internal Reflection Fluorescence Microscopy," in *Methods in Cell Biology*, Chapter 9, vol. 30:245–269, Academic Press, 1989.

Ayers, J. R. et al., "Iterative Blind Deconvolution Method and its Applications," *Optics Letters*, 13:7:547–549, 1988.

Bornfleth, H. et al., "Comparative Genomic Hybridization Imaging by the One–Chip True–Color CCD Camera Kappa CF 15 MC," *Cytometry*, 24:1–13, 1996.

Castleman, K. R. "Color Compensation for Digitized FISH images," *Bioimaging*, 1:159–165, 1993.

Castleman, K. R. "Digital Image Color Compensation with Unequal Integration Periods," *Bioimaging*, 2:160–162, 1994.

Gothot, A. et al., "A Strategy for Multiple Immunophenotyping by Image Cytometry: Model Studies Using Latex Microbeads Labeled with Seven Streptavidin–Bound Fluorochromes," *Cytometry*, 24:214–255 (1996).

Ijdo, J.W. et al., "Improved Telomere Detection Using a Telomere Repeat Probe (TTAGGG)$_n$ Generated by PCR," *Nucleic Acids Research*, vol. 19, No. 17, p. 4780, Sep. 11, 1991, Eynsham, Oxford, GB.

Kawata, S. et al., "Multispectral Image Processing for Component Analysis," *Fluorescence Imaging Spectroscopy and Microscopy*, X. F. Wang, B. Herman eds, J. Wiley & Sons, 1996, pp. 55–86.

LeBeau, M. M. "One FISH, Two FISH, Red FISH, Blue FISH," *Nature Genetics*, 12:341–344, 1996.

(List continued on next page.)

*Primary Examiner*—Constantine Hannaher
*Assistant Examiner*—Darren M. Jiron
*Attorney, Agent, or Firm*—Townsend and Townsend and Crew LLP

[57] ABSTRACT

Techniques for acquiring and analyzing M-FISH images in a manner that allows for proper image registration; and techniques for combining a plurality of registered images to provide labeled images. Epi-illumination embodiments use multiple filter cubes for different subsets of the entire set of desired dyes. The registration problem is addressed by configuring the different multiband cubes so that pairs of cubes have a common dye for which they are configured. Accordingly, a first set of images generated with a first cube includes an image that corresponds to (contains the same features as) one of the images in a second set of images generated with a second cube. This allows the first set of images to be precisely and accurately aligned with the second set of images. A method for generating a labeled image typically includes a normalization of the pixel intensities within each image, followed by a transformation to ratio images.

19 Claims, 11 Drawing Sheets

OTHER PUBLICATIONS

Morris, H. R. et al., "Imaging Spectrometers for Fluroescence and Raman Microscopy: Acousto–Optic and Liquid Crystal Tunable Filters," *Applied Spectroscopy,* 48:7:857–866, 1994.

Patwardhan, A. et al., "Three–Colour Confocal Microscopy With Improved Colocalization Capability and Cross–Talk Suppression," *Bioimaging,* vol. 4(1), pp. 17–24 (Mar. 1996), IOP Publishing Ltd.

Speicher, M. R. et al., "Karyotyping Human Chromosomes by Combinatorial Multi–Fluro FISH," *Nature Genetics,* 12:368–375, 1996.

Speicher, M. R. et al., "Computer Image Analysis of Combinatorial Multi–Fluor FISH," *Biomaging,* vol. 4 (2), pp. 52–64, Sep. 2, 1996, Yale Univ.

Taylor, D. Lansing et al., "Basic Fluorescence MIcroscopy," in *Methods in Cell Biology,* Chapter 13, 29:207–237, Academic Press, 1989.

MULTIFLUOR-FLUORESCENCE IN-SITU HYBRIDIZATION (M-FISH) IMAGING TECHNIQUES USING MULTIPLE MULTIBAND FILTERS WITH IMAGE REGISTRATION

CROSS-REFERENCE TO RELATED APPLICATION

This application claims priority from the following U.S. provisional application, the disclosure of which is incorporated by reference in its entirety for all purposes:

Application Ser. No. 60/029,314, filed Oct. 25, 1996, of Jacques Ginestet, entitled "MULTIFLUOR-FLUORESCENCE IN-SITU HYBRIDIZATION (M-FISH) IMAGING TECHNIQUES USING MULTIPLE MULTIBAND FILTERS WITH IMAGE REGISTRATION."

BACKGROUND OF THE INVENTION

The present invention relates generally to fluorescence microscopy, and more specifically to improvements in image alignment where multiple multiband filters are used in M-FISH techniques.

M-FISH (which stands for multifluor-FISH, multiplex-FISH, multicolor-FISH, or multispectral-FISH) is a technique by which a number of fluorochromes (sometimes referred to as fluorescent dyes, or simply dyes) are used in what is otherwise a standard FISH (Fluorescence In-Situ Hybridization) procedure. A FISH sample is prepared by using multiple probes, each of which binds to a different DNA sequence in the chromosomes in the sample. Each probe is labeled with a different dye or combination of two or more dyes.

A given dye is characterized by an excitation (absorption) spectrum and an emission spectrum. The excitation and emission spectra are also sometimes referred to as the excitation and emission bands. Accordingly when the dye is irradiated with light at a wavelength within the excitation band, the dye fluoresces, emitting light at wavelengths in the emission band. Thus when the sample is irradiated with excitation radiation in a frequency band that excites a given dye, portions of the sample to which the probe labeled with the given dye is attached fluoresce. If the light emanating from the sample is filtered to reject light outside the given dye's emission band, and then imaged, the image nominally shows only those portions of the sample that bind the probe labeled with the given dye.

FIG. 1 is a schematic showing a representative epi-illuminated fluorescence microscope system 5 for generating a single FISH image of a sample 10. The optical arrangement in system 5 includes an excitation filter 12 (shown as one of several such filters on a filter wheel), a dichroic mirror 15, a microscope objective 17 (say 60–100×), and an emission filter 20 (sometimes also referred to as a barrier filter). Excitation radiation from a source 25 passes through excitation filter 12, is largely reflected by dichroic mirror 15 and proceeds through the microscope objective 17 to sample 10. The excitation light traveling toward the sample is shown schematically by hollow arrowheads. Fluorescent radiation emitted from sample 10 passes back through objective 17, through dichroic mirror 15, through emission filter 20 to form an image in an image plane 30. The fluorescent light traveling away from the sample is shown schematically by solid black arrowheads. The image is digitized by a CCD camera 32 and the digitized image is sent to a computer 35 for subsequent processing.

If the filters have single passbands, the particular filters and dichroic mirror are specific to a single dye in the sample. Images for other dyes in the sample are acquired by substituting optical elements configured for the excitation and emission bands for each other dye. The dichroic mirror and the emission filter are typically rigidly mounted to a supporting structure 40 (shown in phantom), often referred to as a cube, with multiple cubes being movable into and out of the optical path. Oppositely directed arrows 42 represent a suitable mechanism such as a rotatable turret or a detented slide mechanism. The multiple excitation filters are typically deployed on a rotatable filter wheel (as shown).

The fact that the different images are produced by moving different cubes into the image path inevitably causes lateral and focus shifts and the like, thereby leading to misregistration of the images. While there are well-known image registration techniques, such techniques tend not to be robust. Since the different images represent fluorescence from different dyes, whose probes are attached to different portions of objects in the sample, attempts to register the images are prone to failure under at least some circumstances.

A number of variations of the instrumentation are well established in the prior art. For example, [Castleman93] discloses the use of a color CCD camera, multiband excitation and emission filters, and a polychroic mirror for simultaneously digitizing emissions from specimens labeled with three fluorescent dyes. The excitation filter passes three narrow bands corresponding to the excitation bands of the three dyes, the polychroic mirror reflects the three excitation bands while transmitting the corresponding emission bands, and the emission filter only passes wavelengths falling within the three emission bands.

As described in [Castleman93], there is significant crosstalk between the fluorescence channels due to the inevitable overlap among dyes' emission spectra and the camera's sensitivity spectra. This is addressed by an image processing step, referred to as color compensation, based on a predetermined knowledge of how each of a given dye's emission is recorded in each of the camera's RGB channels. A 3×3 matrix is determined, and the inverse of this matrix is applied to measured RGB values to eliminate the effect of color spread among the camera RGB channels.

Using a color camera and the multiband filters provides three images with the same cube, and thus avoids the registration problem. On the other hand, color cameras normally provide lower resolution and lower sensitivity than monochrome cameras. [Bornfleth96] compares the traditional technique of acquiring three monochrome images and the technique using a color camera and multiband filters, and concludes that the results are comparable.

The use of a single cube with a color camera is limited to three dyes, however, whereas it is often desired to have more than three dyes. For example, five to seven dyes could provide a significantly larger number of possible combinations. While it may be possible to design a single cube configured for this many dyes, this would create additional challenges to recognize uniquely which dye or combination of dyes contributes to each camera channel. The already stringent optical demands would become even more stringent. It is necessary to have narrowband emission filters since the polychroic mirror typically transmits a small percentage (say 5% to 10%) of the much stronger excitation radiation that is inevitably reflected and scattered from the microscope surfaces and the sample.

While it would be possible to extend the multiband approach of [Castleman93] to more than three dyes by providing two or more multiband cubes and multiband excitation filters, each configured for three dyes, the problem of image registration would again arise.

SUMMARY OF THE INVENTION

The present invention provides techniques for acquiring and analyzing M-FISH images in a manner that allows for proper image registration and yet is easily scaleable for large numbers of dyes. The invention has applicability with epi-illumination and trans-illumination optical systems. The invention further provides techniques for combining a plurality of registered images to provide labeled images.

In short, with respect to epi-illumination embodiments, an aspect of the invention recognizes that it is impractical to configure a multiband filter cube for more than four or five dyes, and therefore takes the approach of having multiple filter cubes for different subsets of the entire set of desired dyes. The invention addresses the registration problem by configuring the different multiband cubes so that pairs of cubes have a common dye for which they are configured. Accordingly, a first set of images generated with a first cube includes an image that corresponds to (contains the same features as) one of the images in a second set of images generated with a second cube. This allows the first set of images to be precisely and accurately aligned with the second set of images.

In a specific embodiment, there are two cubes, each configured for four dyes with one of the dyes being the same for the two cubes. Further, it is preferred to have the dye that is common to the two cubes to be a counterstain that stains all DNA and therefore provides an image with substantially all the objects, thereby allowing the most precise registration. The present invention further contemplates performing color compensation in order to allow accurate quantitative analysis of the images.

This approach allows considerable design flexibility. For example, by selecting a dye that has broad excitation and emission spectra as the common dye between the two cubes, the corresponding bands on the cubes do not have to be as well optimized, thereby allowing the other bands on the cubes to be more fully optimized.

The invention also has applicability for trans-illumination embodiments where multiple multiband emission filters are interposed in the path between the sample and the image plane. The invention addresses the registration problem by configuring the different multiband emission filters so that pairs of filters have a common dye for which they are configured. Accordingly, a first set of images generated with a first multiband emission filter includes an image that corresponds to (contains the same features as) one of the images in a second set of images generated with a second multiband emission filter. This allows the first set of images to be precisely and accurately aligned with the second set of images.

According to further aspects of the invention, a labeled image, i.e., a map of the various dye combinations, is generated from a set of registered color compensated dye images. This could apply to images registered as discussed above, images otherwise registered, or images generated with a single optical setup in the image path, i.e., without interposing multiple interchangeable elements in the image path.

A method for generating a labeled image typically includes a normalization of the pixel intensities within each image, followed by a transformation to ratio images. The latter entails dividing each pixel value in a given normalized color compensated dye image by the sum, taken over the images for all the different dyes, of the pixel values for that pixel position. The ratio images may then be thresholded, and any pixel which is non-zero for a given ratio image can then be considered as having been labeled with the corresponding dye. Each pixel can then be colorized according to the combinations of dyes considered to have labeled that pixel.

A further understanding of the nature and advantages of the present invention may be realized by reference to the remaining portions of the specification and drawings.

DESCRIPTION OF SPECIFIC EMBODIMENTS

1. Overview

Figure 2:
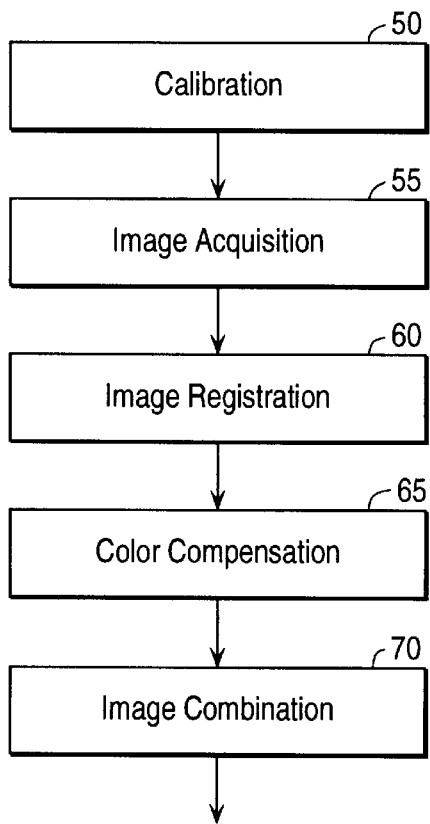
FIG. 2 is a high-level flowchart of a method according to the present invention.

FIG. 2 is a high-level flowchart of a method of generating a set of fluorescence images according to the present invention. The basic steps are shown in a particular order, but some of the steps may be performed in a different order, or portions of different steps may be interleaved.

Figure 1:
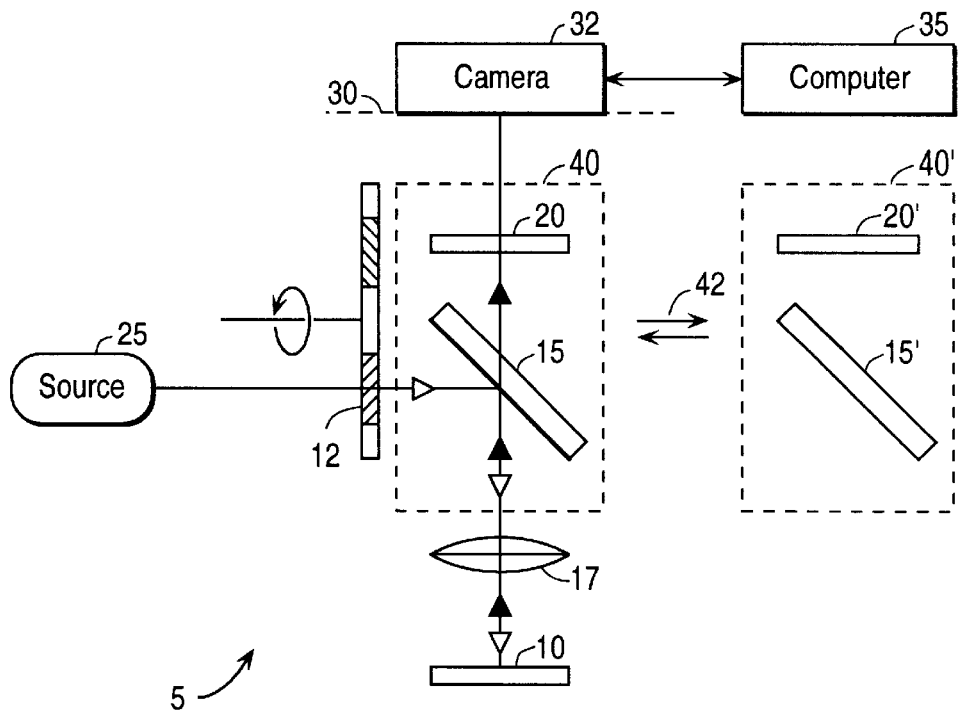
FIG. 1 is a schematic showing a representative epi illuminated fluorescence microscope system within which the invention may be embodied.

The method is performed with apparatus, generally as shown in FIG. 1, except using polychroic mirrors and multiband emission filters configured in accordance with the invention in order to permit desired large number of fluorescent dyes to be used while still permitting accurate image registration among the individual images. The description will be primarily with reference to epi-illumination embodiments which use a wavelength-selective mirror to separate the excitation radiation from the fluorescent emissions from the dyes.

A particular implementation uses an Olympus BX60 microscope, which includes a built-in universal reflected light fluorescence vertical illuminator. Other Olympus models (BX40 and BX50) must be retrofitted with such an illuminator as an add-on accessory. The illuminator, which is located above the microscope objective turret, is configured with an industry-standard dovetail mount to accommodate viewing optics and a camera, and accommodates a cube turret. The microscope and its accessories are available from the Precision Instrument Division of Olympus America, Inc, located in Melville, N.Y. The particular implementation uses a cooled monochrome slow-scan CCD digital camera, marketed under the mark SENSYS, and available from Photometrics Ltd, located in Tucson, Ariz. The particular implementation also uses an excitation filter wheel.

In short, the invention uses a plurality of N multiband cubes, each comprising a polychroic mirror and a multiband emission filter. Each cube is configured for an associated one of N subsets of the total set of dyes, with the $i^{th}$ subset having a plurality of $M_i$ distinct dyes (i ranges from 1 to N). The subsets are chosen so that the $j^{th}$ subset and the $(j+1)^{th}$ subset have one dye in common, referred to as the $j^{th}$ common dye (j ranges from 1 to N−1). In a specific embodiment, a given polychroic mirror has passbands matched to the emission spectra of the dyes in the associated subset, while reflecting light at the wavelengths used for excitation. The associated multiband emission filter also has passbands matched to the emission spectra of the dyes in the associated subset.

The excitation filters are matched to the reflection bands of the polychroic mirrors, which are matched to excitation spectra of the set of dyes. Since the excitation filters are not disposed in the path from the sample to the image plane, separate single-band filters can be used without raising image registration problems.

In possible alternative embodiments, the polychroic mirror would be configured to transmit light at the wavelengths used for excitation, and to reflect light at the wavelengths at which the dyes emit. In such embodiments, the associated multiband emission filter would still have passbands matched to the emission spectra of the dyes in the associated subset, but this would correspond to the reflection bands of the associated polychroic mirror. Similarly, the excitation filters would still be matched to excitation spectra of the set of dyes, but this would correspond to the transmission bands of the polychroic mirrors.

A calibration procedure 50 is performed to develop a set of parameters that can be used in a later processing step (color compensation) used to account for the fact that emissions from one dye show up in an image that is nominally intended to contain only objects labeled with a different dye. Put another way, in an ideal world, when the excitation filter for a given dye is in place, the resultant image would only show portions of the sample that bind the probe labeled with the given dye. However, as described above, there is cross-talk, and it is preferred to process the images to correct for such cross-talk. This is discussed in detail below in a section entitled "Color Compensation."

This is followed by an image acquisition phase 55 where images nominally corresponding to the different dyes are produced. An image for a given dye is generated by using the cube associated with that dye's subset and the appropriate excitation filter. It is noted that multiple images will be acquired for each dye that is a common dye. Corrections such as a darkfield correction may be applied to the images prior to further processing of the images.

The sets of images taken with the different cubes are then subjected to an image registration step 60 that makes use of the images for the common dyes. The images, so registered, are then subjected to a color compensation step 65, which makes use of the color compensation calibration information to correct pixel values in each image so that they represent, as well as is practical, the presence or absence of emission from that image's corresponding dye. The color compensated images are sometimes referred to as pure dye images. The registered and color compensated images are then preferably combined at a step 70 that provides a map of the various dye combinations.

The apparatus typically operates under computer control to ensure proper energization of the light source, stepping the cube turret and the excitation filter wheel, and operating the camera. The computer that controls the apparatus may be the same computer that processes the images.

2. Dye Characteristics

From a theoretical point of view, the choice of a set of dyes requires only that the dyes have distinguishable excitation and emission spectra. A possible criterion is that at any given pair of dyes have to have excitation peaks or emission peaks that differ by more than some threshold amount (say 20 nm), defined by the filters' capabilities to differentiate.

From a practical point of view, the dyes are more or less imposed by molecular biology constraints. For example, in [Speicher96] the dyes of choice are DAPI, FITC, Cy3, Cy3.5, Cy5, Cy5.5, and Cy7. Approximate values of their respective excitation and emission maxima are summarized in the table below:

| Dye (fluorochrome) | Excitation Peak | Emission Peak |
|---|---|---|
| DAPI | 350 | 450 |
| FITC | 490 | 520 |
| Cy3 | 550 | 570 |
| Cy3.5 | 580 | 595 |
| Cy5 | 650 | 670 |
| Cy5.5 | 680 | 700 |
| Cy7 | 755 | 780 |

Figure 3A:
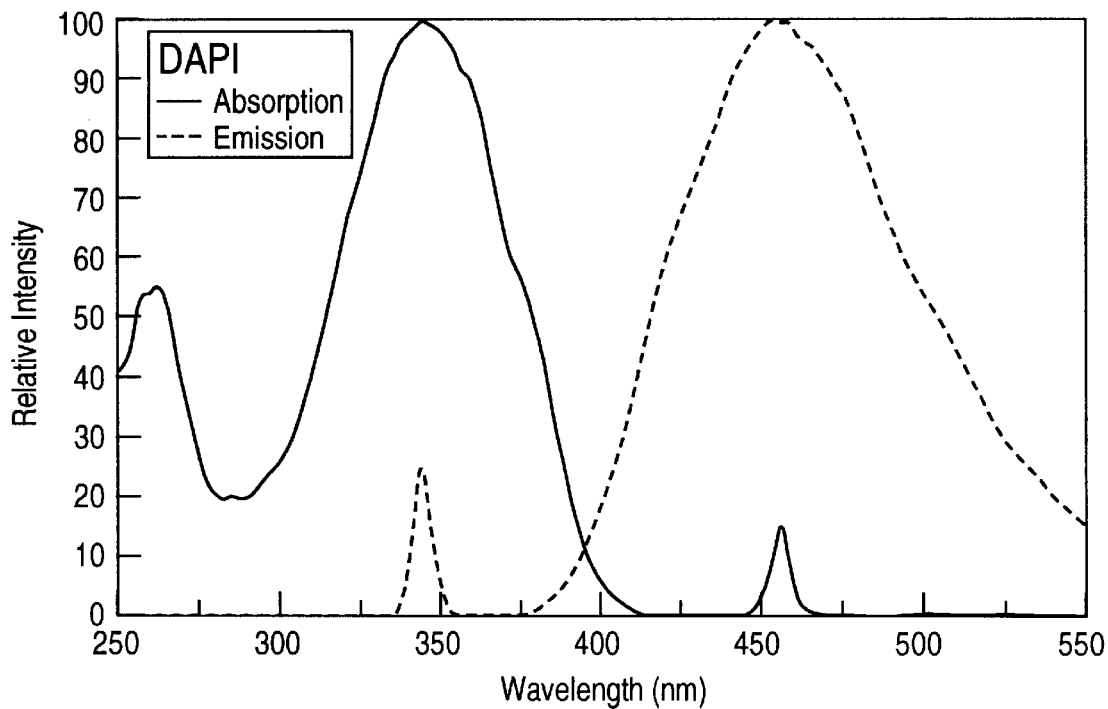
FIGS. 3A–3G show the excitation and emission spectra for seven representative fluorescent dyes.
Figure 3B:
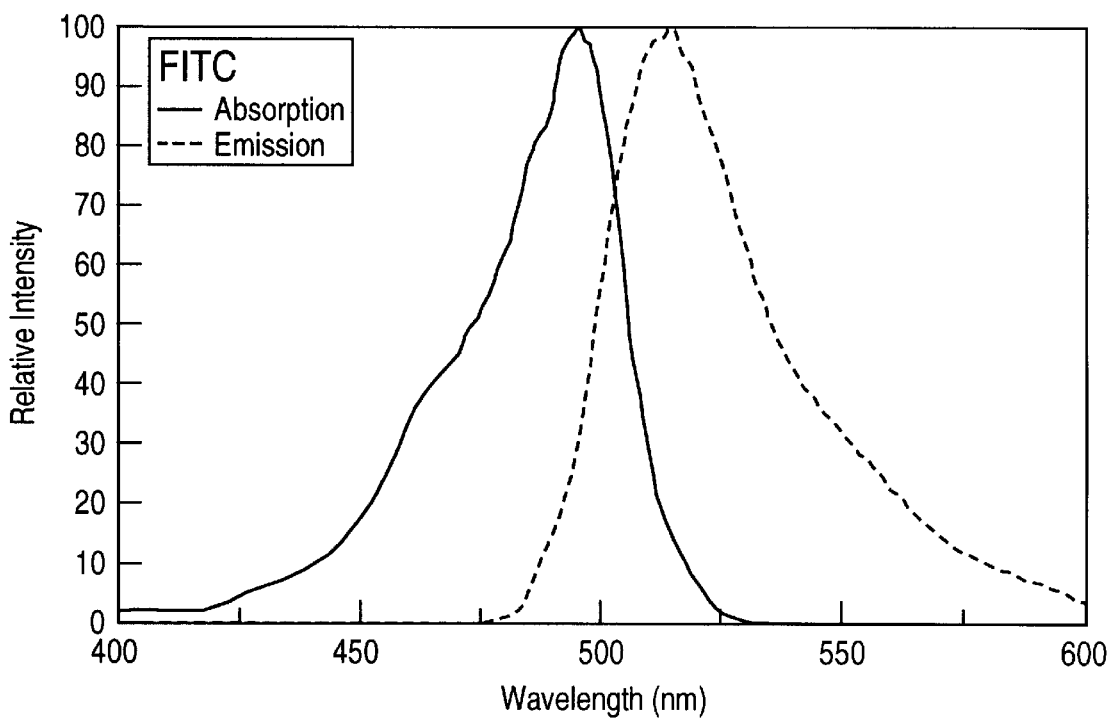
Figure 3C:
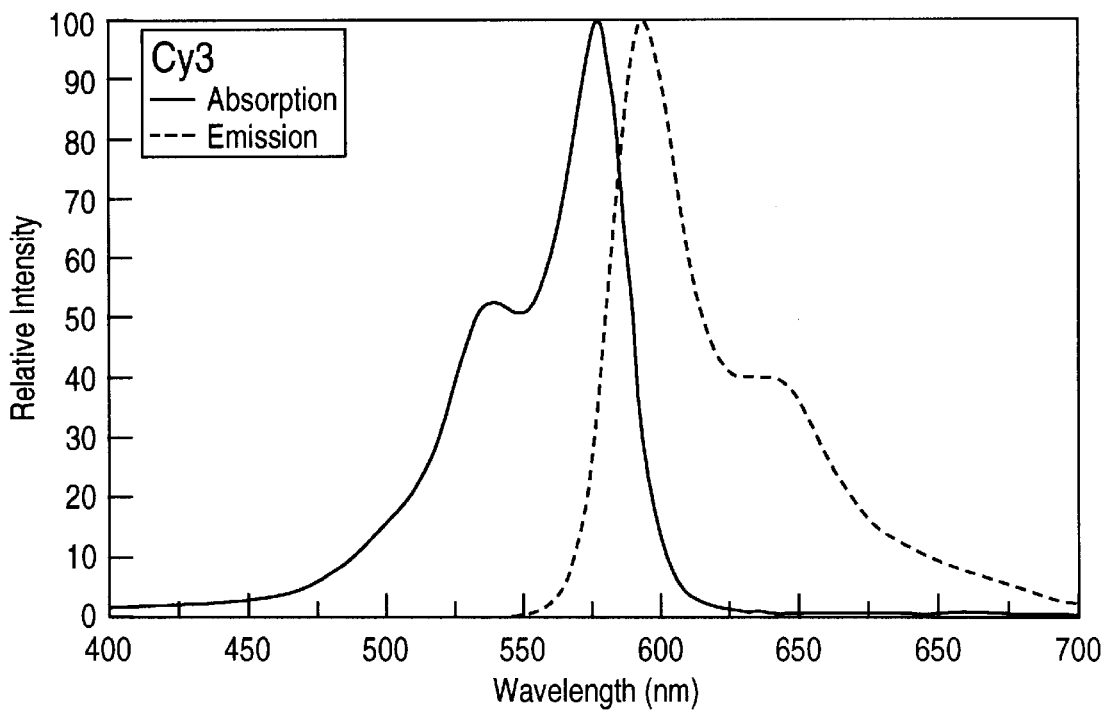
Figure 3D:
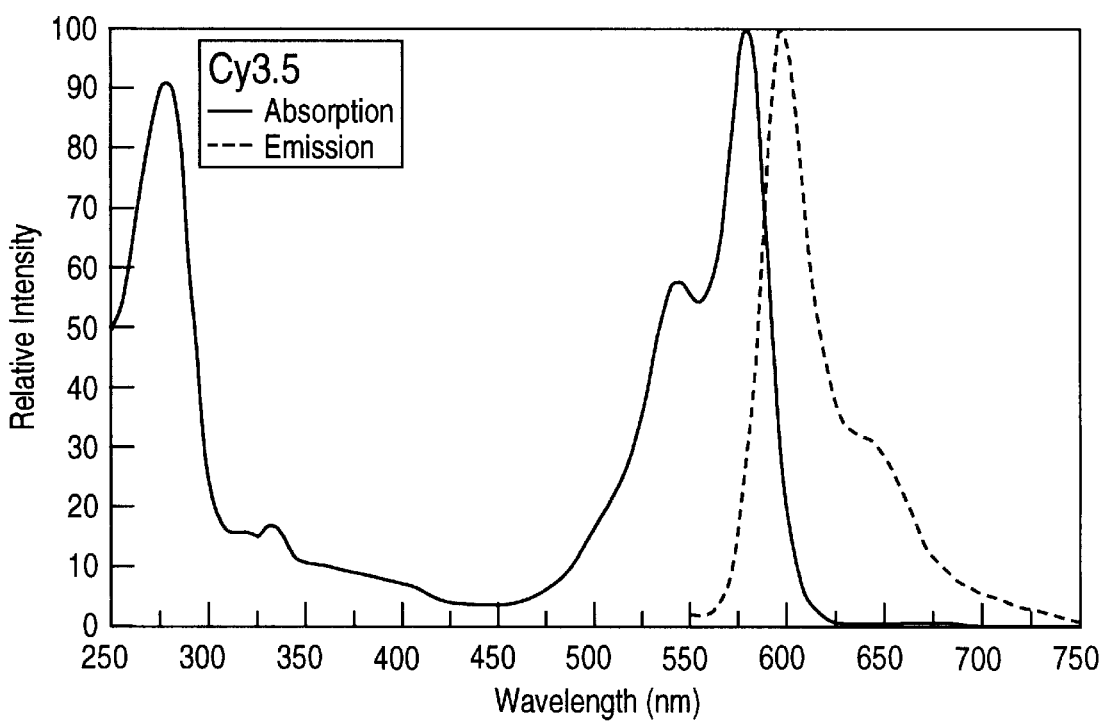
Figure 3E:
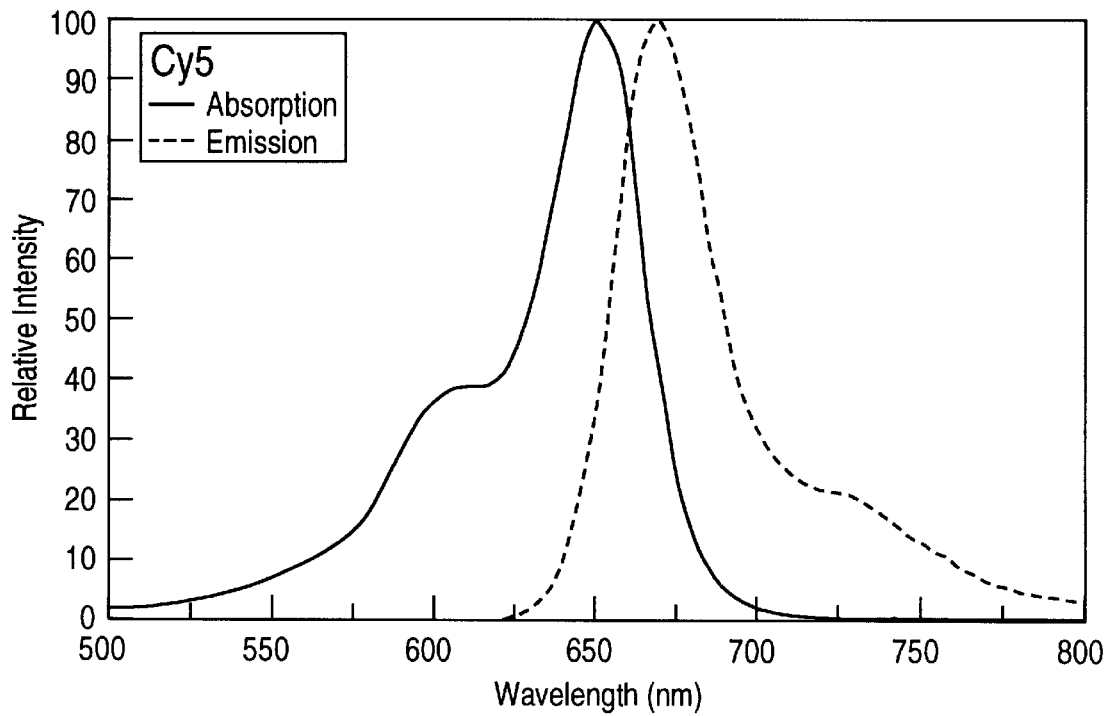
Figure 3F:
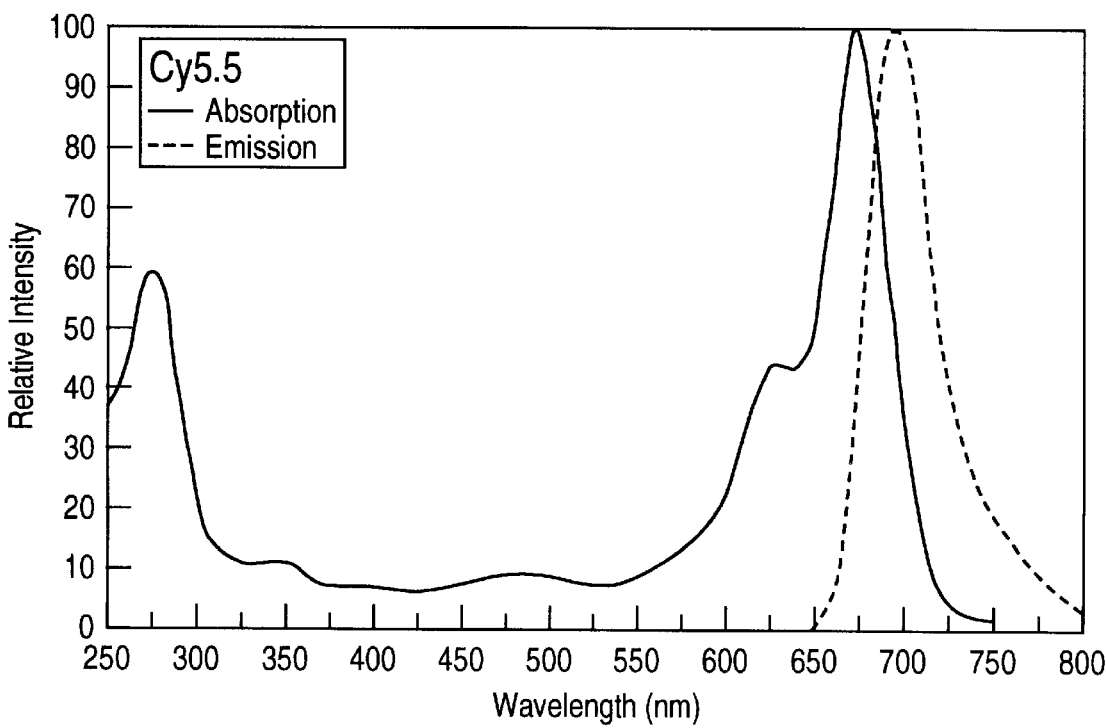
Figure 3G:
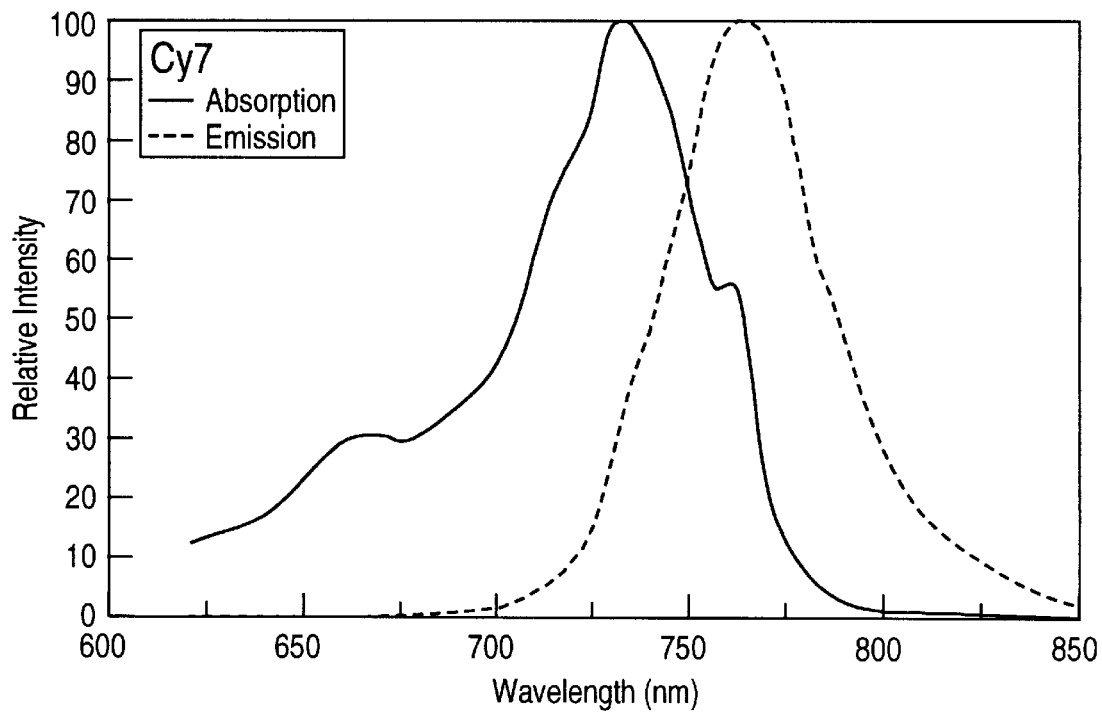
Figure 3H:
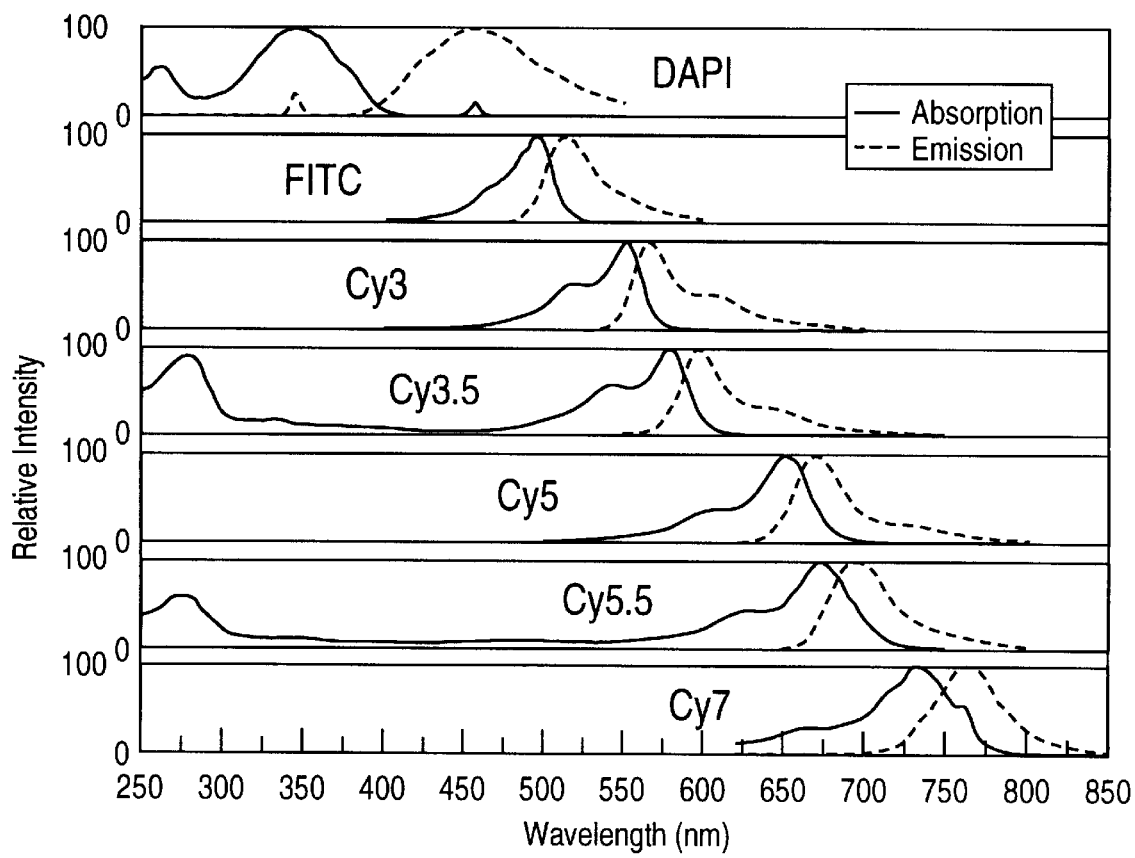
FIG. 3H shows a composite view of the spectra.

FIGS. 3A–3G show the excitation and emission spectra for these representative fluorescent dyes. FIG. 3H shows the spectra juxtaposed on a single plot. The emission spectrum of a dye is substantially independent of the excitation wavelength used to excite the dye, but for efficiency's sake, it is preferred to excite the dye with a range of wavelengths near the maximum in the excitation spectrum.

These dyes have to be treated pretty much as a given of the M-FISH problem. However, the wet preparation (namely the concentrations of the various dyes) still is preferably adjusted so that the various dyes, as observed through the chosen filters, have reasonable brightnesses (i.e., require reasonable exposure times). Furthermore, the relative total brightness of each dye, as observed with the selected sets of filters, is preferably roughly equal to that of the other dyes (say within a factor of 2 or 3) so as to avoid one signal overpowering the others (issues of dynamic range, non-linearity, saturation, etc).

Figure 4A:
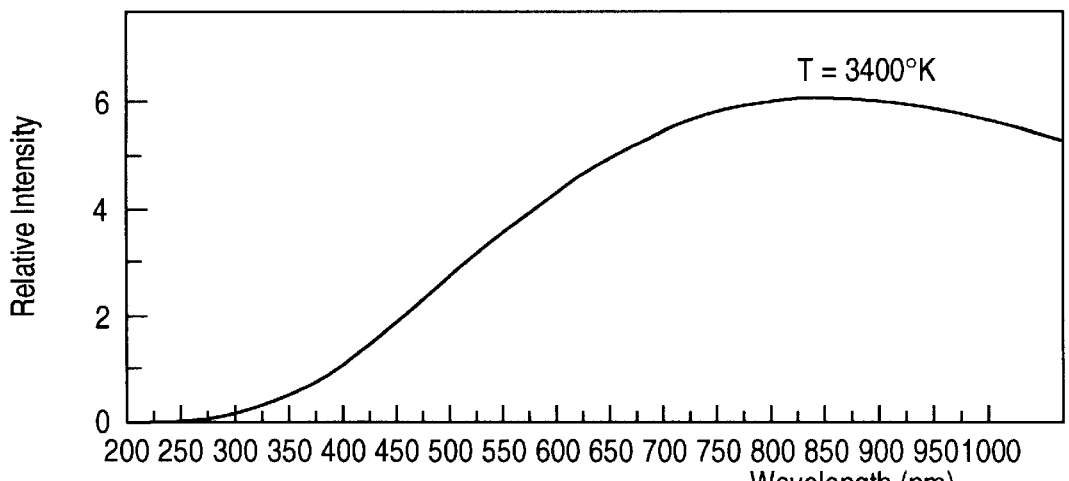
FIGS. 4A–4C show relative spectral outputs of tungsten, xenon, and mercury lamps.
Figure 4B:
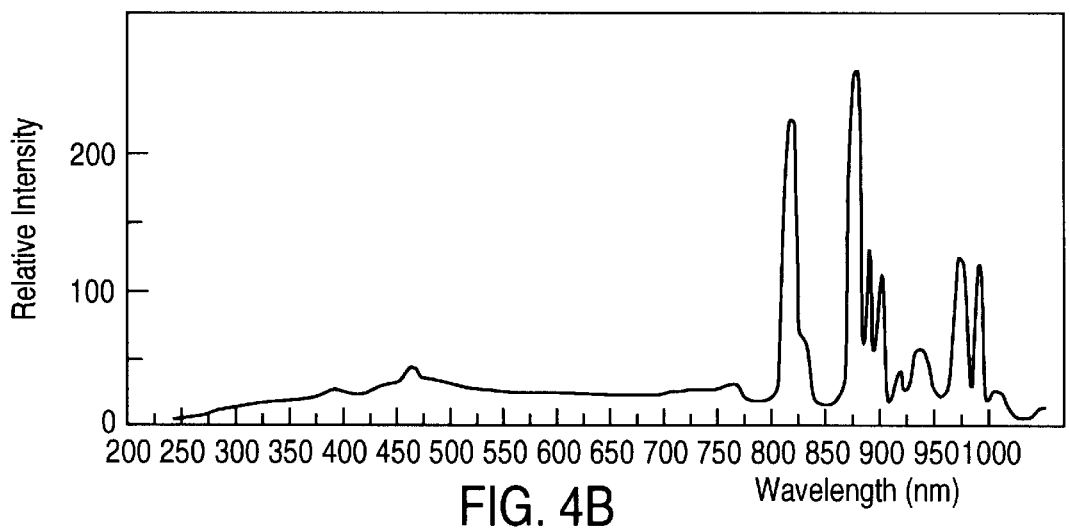
Figure 4C:
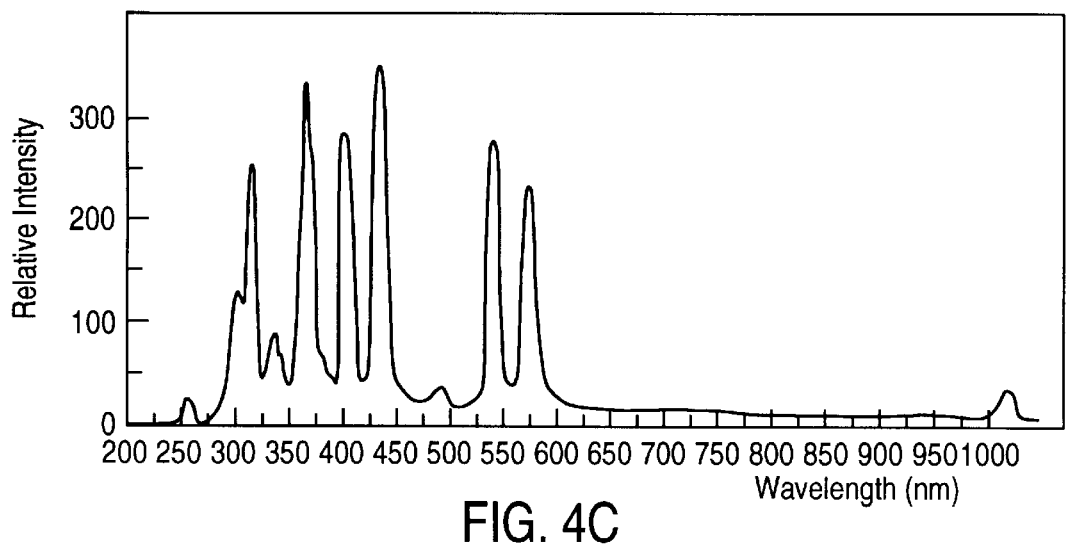

FIGS. 4A–4C show relative spectral outputs of tungsten, xenon, and mercury lamps. The choice of excitation light source is practically limited to mercury or xenon arc lamps; mercury is brighter, while xenon has a more uniform spectrum. A priori, xenon would be preferable because of the large numbers of dyes to be used. A 150 W lamp is preferred to compensate for the lower output efficiency, although a 75 W xenon lamp may be sufficient. The lamp is preferably provided with a filter to block IR above 800 nm.

3. Cube Characteristics

As can be seen from the spectra in FIGS. 3A–3G, most of the dyes (DAPI is an exception) have their excitation peaks close to their emission peaks. Further, the emission peak of one dye tends to be close to the excitation peak of another. Accordingly, the design of a single cube that passed the emissions from the seven dyes while blocking/reflecting the excitation light would be extremely difficult (requiring very narrow passbands). On the other hand, if one has to deal with only a subset of the dyes at a time, the design constraints are considerably relaxed.

Figure 5A:
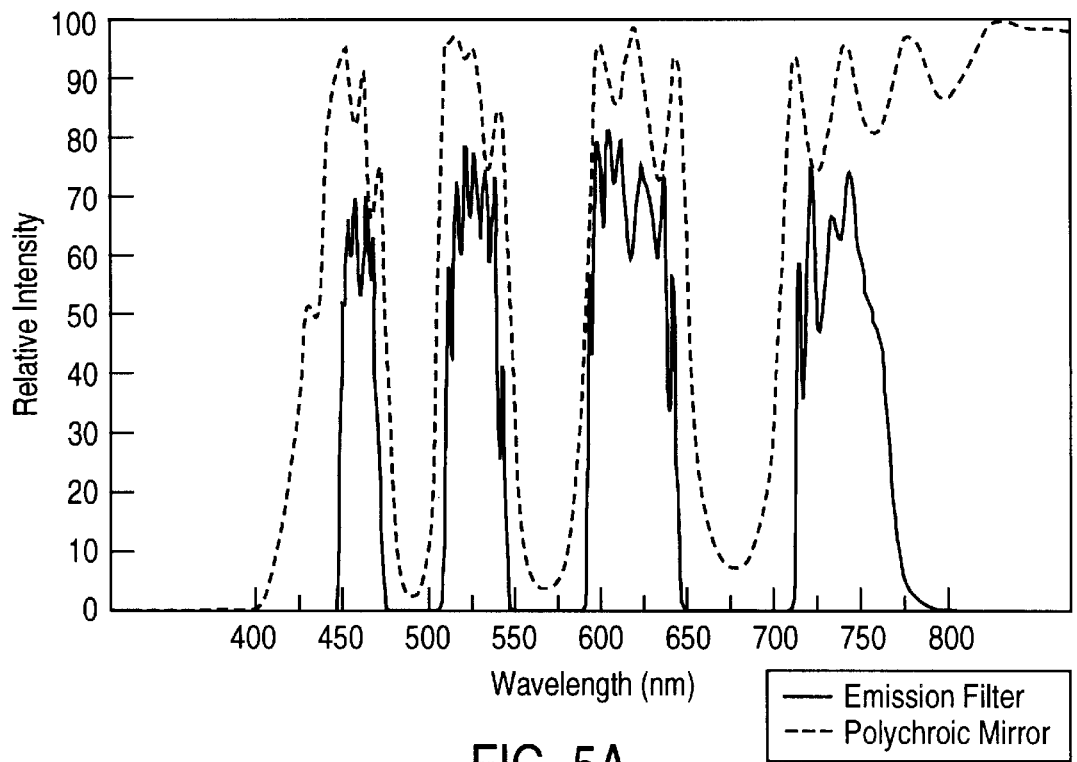
FIG. 5A shows the bandpass spectra for the polychroic mirror and the emission filter in a first one of the cubes according to the invention.
Figure 5B:
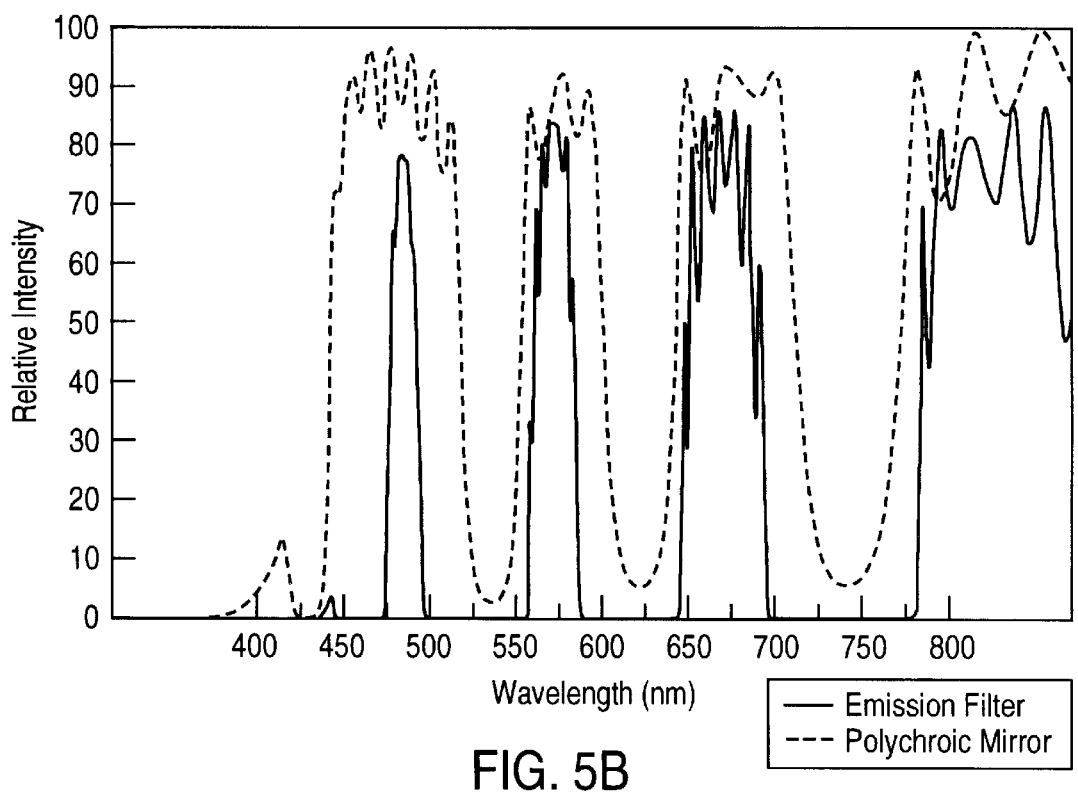
FIG. 5B shows the bandpass spectra for the polychroic mirror and the emission filter in a second one of the cubes according to the invention.

FIG. 5A shows the bandpass spectra for the first cube's polychroic mirror (heavier line with troughs that exhibit non-zero transmission between transmission peaks) and the emission filter (lighter line, with substantially zero transmission between peaks); FIG. 5B shows the second cube's spectra. The first cube is configured for the subset of dyes consisting of DAPI, FITC, Cy3.5, and Cy5.5, while the second cube is configured for the subset of dyes consisting of DAPI, Cy3, Cy5, and Cy7.

DAPI is the common dye. One point to note in the specific design is that the emission filters for DAPI are at different wavelengths in the two cubes (450–470 nm in the first cube and 475–490 nm in the second). This exploits DAPI's broad emission band, allowing flexibility in the placement of the DAPI band, thereby allowing better placement of the bands for the other dyes in each of the subsets.

The excitation filters are preferably implemented as a set of single-band filters (e.g., interference filters), which allows a given filter to pass excitation light in a very precise and narrow band (say 10–20 nm). The excitation filters should be matched to the set of cubes in the sense that the excitation light passed by a filter should not be within the passband of a cube with which it is to be used. Since the passband of a cube is ultimately defined by the emission filter passbands for that cube, this means that the excitation filters' passbands cannot overlap the emission filters' passbands.

In embodiments where the polychroic mirrors pass the excitation light and reflect the fluorescent emissions, it is still true that the excitation filters' passbands cannot overlap the emission filters' passbands. However, in such cases, the emission filters' passbands will fall outside the polychroic filters' passbands and the excitation filters' passbands will fall within the polychroic mirror's passbands.

It is in principle possible to use the same excitation filter with more than one cube if two dyes associated with different cubes have sufficiently close excitation spectra. The dyes should have sufficiently different emission spectra that each dye's emissions will be passed only by that dye's associated cube.

Note that the polychroic mirrors do not reflect 100% of the excitation light, as evidenced by the fact that their transmission never falls to zero in the regions between the passbands. This makes it important to have the associated multiband emission filter, whose transmission falls substantially to zero (say less than $10^{-4}$) between the passbands.

There is a tradeoff between the number N of different cubes and the number of dyes for which each cube is configured. In the specific embodiment, where there are seven dyes, there are two cubes, each configured for four dyes (including the common dye). It is feasible to design a cube for four dyes; it is much more difficult to design a cube for seven dyes. While it would be even easier to optimize a cube for two dyes, that would lead to an excessive number of cubes.

When there are more than two cubes, the issue arises whether the same common dye should be used for more than two adjacent pairs. This is typically a design choice. Repeating a dye more than once could have the effect of necessitating more cubes, but there may be reasons to prefer a certain dye as the common dye between more than one adjacent pair. In the specific embodiment, the common dye is DAPI, which is a counterstain that stains all DNA. This means that the DAPI image in each set of images contains the most objects, and makes the registration even more robust. Further, DAPI has broader excitation and emission spectra, which relaxes the design constraint on the cubes, making it easier to optimize the cube for the other dyes in each subset.

4. Image Acquisition and Correction

Figure 6:
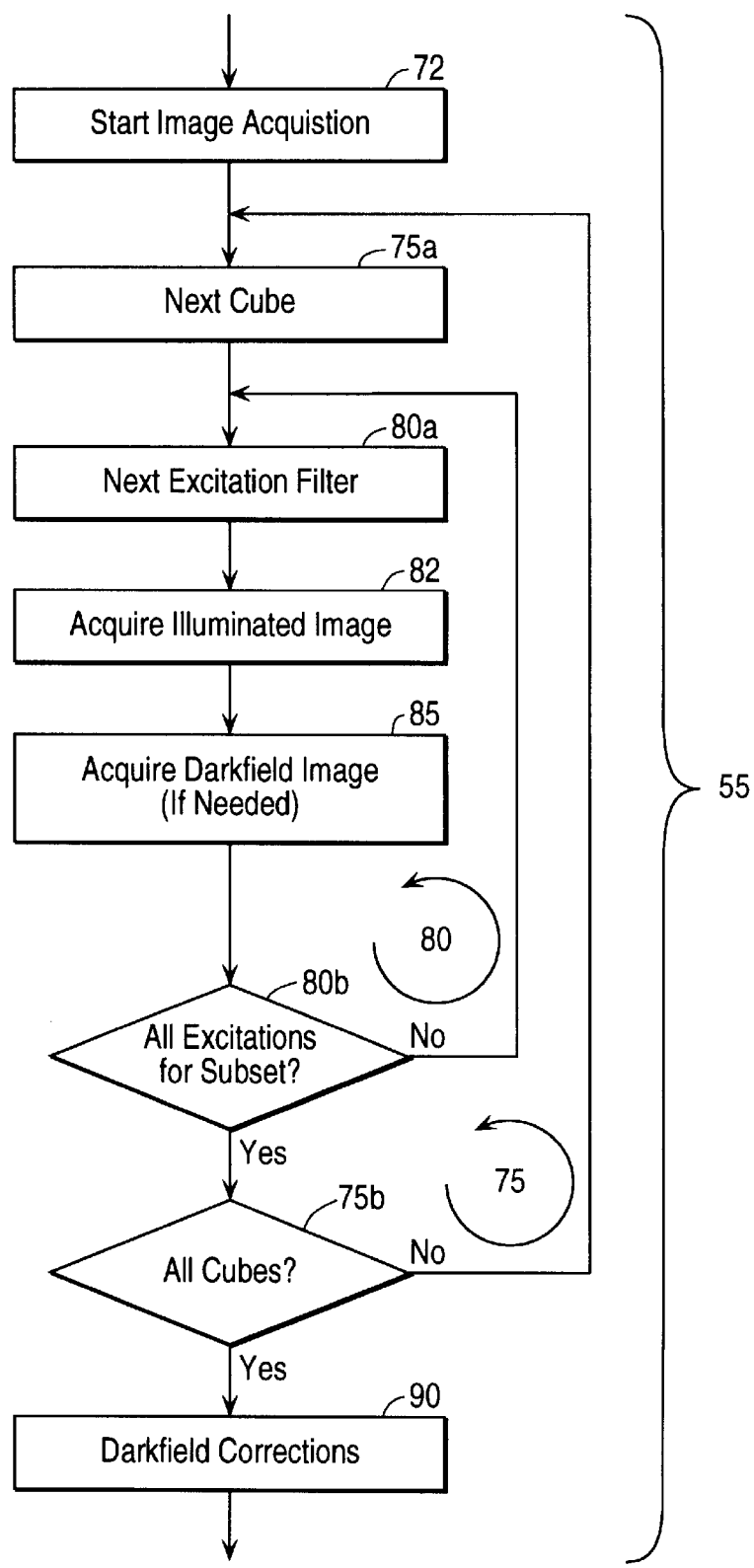
FIG. 6 is a flowchart showing additional details of the image acquisition step shown in FIG. 2.

FIG. 6 is a flowchart showing additional details of image acquisition step 55 (shown in FIG. 2). The image acquisition commences (step 72), and, as noted above, entails sequencing through the cubes (outer loop 75, bounded by step 75a and branch 75b) and, for each cube, sequencing through the excitation filters for the cube's associated dye subset (inner loop 80 bounded by step 80a and branch 80b). Thus, the image acquisition step preferably includes, for values of i from 1 to N, illuminating the sample through an appropriate one of the excitation filters and the $i^{th}$ polychroic mirror, and directing light emanating from the sample to the camera along an optical path that includes the $i^{th}$ polychroic mirror and the $i^{th}$ emission filter. Thus each of the images in the plurality of $M_i$ images corresponds to a respective one of the $M_i$ distinct dyes. The acquired image is referred to as an illuminated image, and its acquisition is shown schematically as a step 82.

It is preferred to perform a darkfield correction on the acquired images to account for "hot" pixels in the camera and dark current. This entails acquiring images with no illumination (step 85), typically effected by turning the source off and having one of the positions on the excitation filter wheel being opaque so as to act as a shutter. These images, referred to as darkfield images, are subtracted from the illuminated images (step 90). Each darkfield image is preferably characterized by the same acquisition parameters (exposure time and digitization parameters) as the illuminated image from which it is subtracted. If these parameters are the same for all illuminated images for a given cube, only one darkfield image need be acquired for the cube, and subtracted from all the illuminated images for that cube. At the other extreme, where the acquisition parameters are different for the different images for a given cube, it is preferable to acquire multiple darkfield images. The possibility of acquiring only a single darkfield image for a set of illuminated images for a given cube is represented in the figure by the parenthetical notation "if needed."

While the flowchart shows the darkfield corrections being performed after all the images are acquired, there may be advantages to interleaving the image acquisition and darkfield correction. For example, storage requirements could be reduced if the darkfield image were to be subtracted from its corresponding illuminated image as soon as the two images are available. Depending on the processing power of the computer, this may be possible without unduly prolonging the image acquisition step. On the other hand, if the image processing is to be offloaded to another computer, it may be preferred to shorten the image acquisition step by doing all the darkfield corrections after the images are acquired (as shown in the figure).

5. Image Registration

Figure 7:
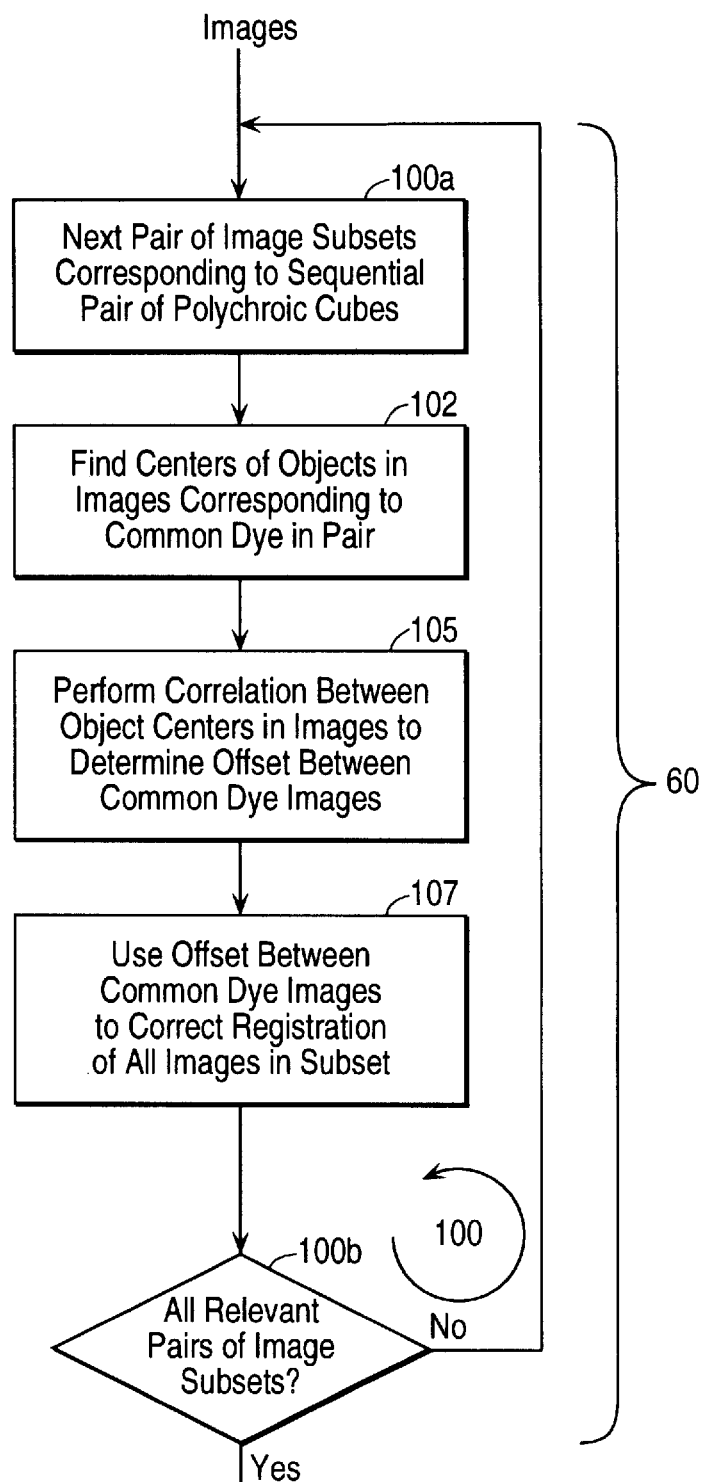
FIG. 7 is a flowchart showing additional details of the image registration and image combination steps shown in FIG. 2.

FIG. 7 is a flowchart showing additional details of image registration step 60. As discussed above, image registration between the $M_j$ images taken with the $j^{th}$ cube and the $M_{j+1}$ images taken with the $(j+1)^{th}$ cube relies on the fact that each set includes an image taken with a filter set configured for the same (common) dye. This ensures that the two images contain the same objects, thereby making image correlation techniques very robust. It is convenient to number the different subsets in a linear array with each one of (N−1) adjacent pairs sharing a common dye. Thus the first and second subsets share a common dye, the second and third subsets share a common dye, etc. Equivalently, since the cubes are uniquely associated with the subsets of dyes, the cubes can be thought of as defining (N−1) adjacent pairs.

The image registration begins by selecting the relevant subsets of images (preferably darkfield corrected), namely those having been taken with adjacent pairs of the cubes. The image registration thus entails sequencing through the subsets of images for adjacent pairs (loop 100, bounded by step 100*a* and branch 100*b*). For each adjacent pair, the images corresponding to the common dye are registered. In a specific embodiment, this entails finding the centers-of-gravity of the objects in the common dye images (step 102), and determining a set of registration parameters that provide the best correlation between the sets of object centers (step 105). This correlation may be a least squares fit. In a current embodiment, x and y translational offsets provide adequate registration; other embodiments could benefit from determining additional parameters representing rotation, magnification, and skew.

Once the offset between the common dye images is determined, the offset values are applied to all the images in one of the subsets to register them to the images in the other subset (step 107). Once all the image subsets have been registered, the images are color compensated to produce the images can be combined in any desired manner to determine which portions of the sample contain various ones of the set of fluorescent dyes.

6. Color Compensation

Color compensation has been outlined in general terms in [Castleman93] and [Castleman94]. (See also [Bornfleth96] for a somewhat different treatment). Given the actual emission spectra of the selected dyes, and the actual sensitivity spectra of the selected filter sets (and, to a lesser degree, of the camera), it is generally impossible to obtain complete isolation of each dye. Put another way, one cannot obtain images representative of only a single dye; spectral overlap spreads each dye's contribution across the various images.

Consider, for the sake of simplicity, the case of three dyes; the following discussion can easily be extended to any number of dyes. Assume that for such preparations, there are three different filter sets ($S_1$, $S_2$, $S_3$), i.e., sets of matched excitation, dichroic and emission filters.

If a sample contains only dye $F_1$, and is imaged with each of the three filter sets, there are three resulting images ($I_{11}$, $I_{21}$, $I_{31}$). For each pixel, it is possible to compute the intensity ratios between images (i.e., $I_{11}(i, j)/[I_{11}(i, j)+I_{21}(i, j)+I_{31}(i, j)]$), and then compute the average over all pixels above a certain threshold (to avoid signal-to-noise problems, divide-by-zero problems, etc). This gives three factors ($C_{11}$, $C_{21}$, $C_{31}$) representing the proportion of emissions from dye $F_1$ which made its way through the various filters sets (note that ($I_{11}+I_{21}+I_{31}=1$). Similarly for dyes $F_2$ and $F_3$, one obtains ($C_{12}$, $C_{22}$, $C_{32}$) and ($C_{13}$, $C_{23}$, $C_{33}$) respectively.

It is possible to define a matrix C, the color spread matrix, where each element $C_{ij}$ represents the proportion of the total measured brightness of emissions from dye i which was observed by filter set j:

$$C = \begin{array}{c} \phantom{x} \\ \begin{array}{|ccc|} \hline C_{11} & C_{12} & C_{13} \\ C_{21} & C_{22} & C_{23} \\ C_{31} & C_{32} & C_{33} \\ \hline \end{array} \end{array} \begin{array}{c} F_1\ F_2\ F_3 \\ \begin{array}{c} S_1 \\ S_2 \\ S_3 \end{array} \end{array}$$

Note that the columns of C sum to 1; this is intuitively desirable, so that the discussion can be in terms of percentages, but is actually not required; the only thing required is that the coefficients be independent of absolute intensity and representative of relative intensities.

Then, if one images a preparation containing all three dyes, for each pixel, given the true dye amounts present at that point ($f_1,f_2,f_3$), one would measure the values ($i_1,i_2,i_3$) such that $$\begin{vmatrix} C_{11} & C_{12} & C_{13} \\ C_{21} & C_{22} & C_{23} \\ C_{31} & C_{32} & C_{33} \end{vmatrix} * \begin{vmatrix} f_1 \\ f_2 \\ f_3 \end{vmatrix} = \begin{vmatrix} i_1 \\ i_2 \\ i_3 \end{vmatrix} \text{ or } I = C * F \quad [\text{Eq. 1}]$$

And therefore $$F=C^{-1}*I \quad [\text{Eq. 2}]$$

That is, if, at each pixel, the observed vector I is multiplied by the inverse of the color spread matrix, $C^{-1}$, called the color compensation matrix, the true dye brightness values are recovered.

Obviously, this technique will work if C is well conditioned; that is if C can be inverted, and if the solution is stable with respect to small variations of the observed values or of the coefficients of C. Such a case can be tested by doing a singular value decomposition (SVD) of C [Press92]. Note that in the case of square matrices (which C is), singular values and eigenvalues are essentially the same thing.

Briefly stated SVD is based on the fact that any M×N matrix whose number of rows M is greater or equal to its number of columns N can be written as the product of an M×N column-orthogonal matrix U, an N×N diagonal matrix W with positive or null elements (the singular values), and the transpose of an N×N orthogonal matrix V. That is, $$C=U*W*V^T \quad [\text{Eq. 3}]$$

where:

W is diagonal, with each $w_i \geq 0$;

$U^T*U=V*V^T=V^T*V=1$ (orthogonal conditions); and 1 is the identity matrix.

It follows that $$C^{-1}=V*W'*U^T \quad [\text{Eq. 4}]$$

where W' is diagonal, with each $w'_i=1/w_i$.

Obviously, this is defined only if all the singular values are non-zero; in such case, C is called non-singular, and a unique solution can be obtained:

$$F=V*W'*U^T*I \quad [\text{Eq. 5}]$$

If some of the singular values are very small, then C is said to be ill-conditioned, and even though an inverse exists, the solutions are unstable (i.e., a small change in the observed values I creates a large change in the calculated values F). However, even in such a case, if C is singular (one or more of its singular values is zero) or ill-conditioned (one or more of its singular values is very small), one can find the solution which minimizes the residual |C.F-I|; this is not "the" unique solution (which does not exist in such a case), but is often as good. It is obtained by using a modified matrix W", where $1/w_i$ is replaced by zero if $w_i$ is zero (or very small). In this case, this solution, optimal in the least square sense, is given by:

$$F=V*W''*U^T*I \quad [\text{Eq. 6}]$$

Therefore, it is preferred to perform a SVD on C, to eliminate null or very small singular values, and to then solve [Eq. 6] for the solution which minimizes the residual ([Press92], page 62).

In terms of computation times, note that this SVD needs to be computed only once; thereafter, only a direct matrix multiplication needs to be performed (albeit for each pixel). As an order of magnitude, performing a N×N matrix multiply at each pixel, will require about as much computing power as performing an N×N convolution of the image (hence a few seconds to tens of seconds for values of N around 7). Algorithms for the SVD (and even source code) are readily available (e.g., [Press92]).

Finally, it will be evident that this whole approach can easily be extended to any number N of dyes, simply by observing them with an equal number N of filter sets (thus giving a N×N color spread matrix). Actually, one could use M filter sets, with M>N; this would give an overdetermined problem, but one that could potentially be much more stable than with M=N. Such an overspecified can be solved by the very same SVD technique [Press92].

The color spread matrix (and hence the color compensation matrix) depends on the dyes, the filter sets, the lamp used for excitation, and the camera. Recalibration is generally needed if any of them changes. This is because such changes are non-linear (i.e., do not affect all raw images identically) and are uncalibrated (i.e., there is no analytical expression of these changes). Thus it is generally difficult to account for this in the set of linear equations.

It should be noted that the determination of the color spread matrix will require the acquisition of $N^2$ images (where N is the total number of dyes used; five to seven in practice, thus 25 to 49 images to capture). However, the total number of images to acquire for calibration can be reduced to N if a calibration scene containing easily identifiable single-labeled chromosomes can be obtained. Such a scene would contain some chromosomes labeled with only dye $F_1$, some labeled with only dye $F_2$, etc, each easily identifiable by means other than their color.

7. Image Combination

In the case of M-FISH, one is normally interested in generating a labeled image, i.e., a map of the various dye combinations. There are a number of ways to approach this. In essence, what is desired is to determine, for each pixel position, which of the pure dye images has a sufficient contribution to signify the presence of that dye at the corresponding site in the sample.

Figure 8:
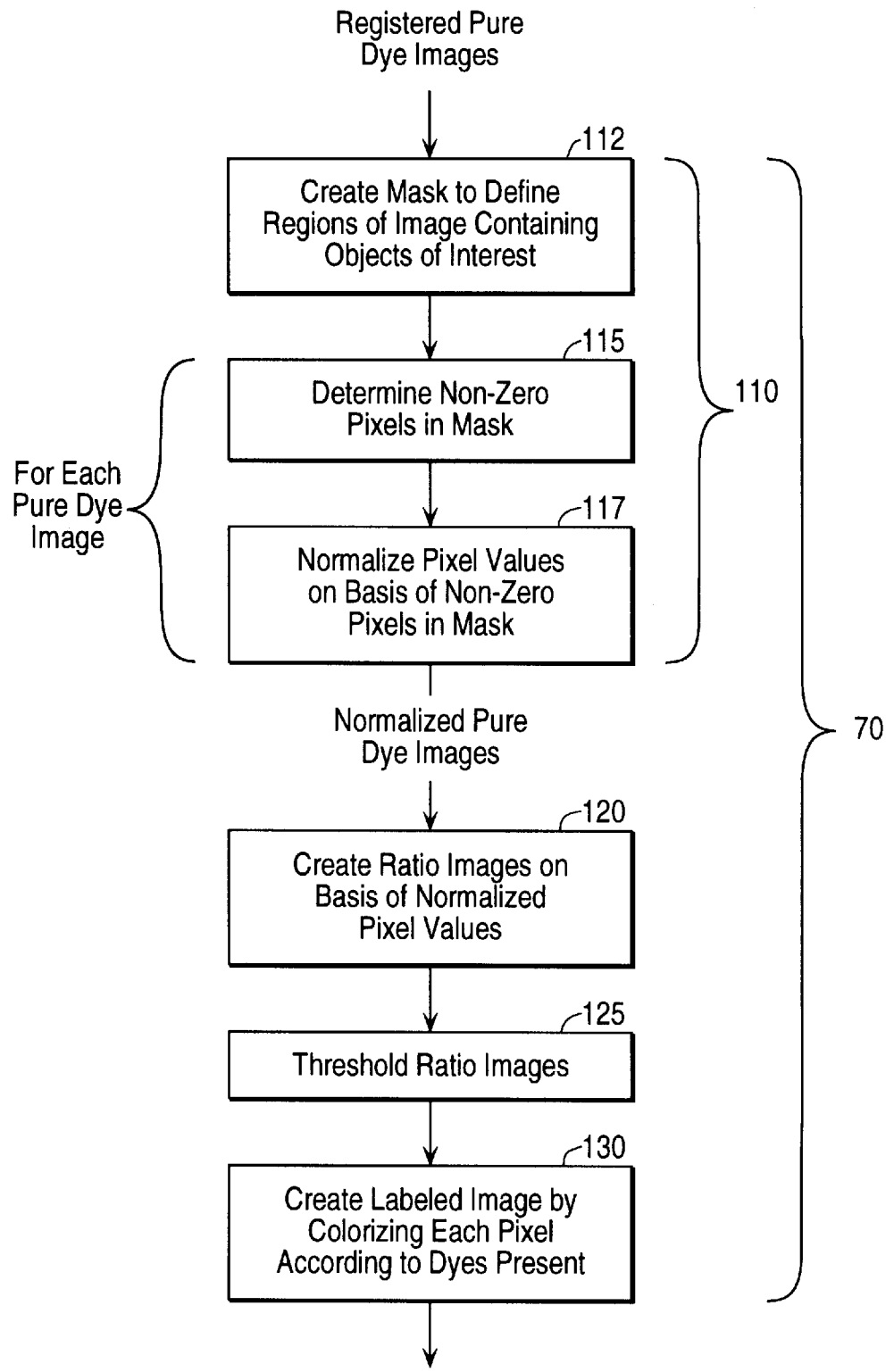
FIG. 8 is a flowchart showing additional details of the image combination step shown in FIG. 2.

FIG. 8 is a flowchart showing additional details of image combination step 70 shown in FIG. 2. In the case of M-FISH, one is normally interested in generating a labeled image, i.e., a map of the various dye combinations. There are a number of ways to approach this. In essence, what is desired is to determine, for each pixel position, which of the pure dye images has a sufficient contribution to signify the presence of that dye at the corresponding site in the sample.

One approach is simply to threshold the color compensated pure dye images, and then, for each pixel position, determine which pure dye images have a non-zero value at that pixel position. This approach is simple, but it may be difficult to determine an appropriate threshold when the images differ in intensity. Differences in intensity can arise as a result of a number of factors, including the vagaries of wet preparation and possible non-uniformity of illumination.

Accordingly, it is generally preferred to perform some sort of normalization (step 110) before determining the relative values of the different images at a given pixel position. One approach to normalization is, for each pure dye image, to determine the maximum value in that image, and then normalize the pixels in that image to the maximum value in that image. This technique may be susceptible to spurious objects in the image, and so may be refined by normalizing each image to its average pixel value.

A preferred technique for normalizing the pure dye images is to base the normalization on pixels that correspond to objects of interest in the images (i.e., chromosomes in the M-FISH case). This is done by creating one or more masks (step 112) representing locations (i.e., having ON pixels) where there are expected to be objects. While finding the objects in the general case could entail significant image processing, it is facilitated in the special case where one of the dyes is DAPI, which stains all chromosomes. As described above, DAPI is preferably one of the dyes, and indeed the dye used for the common dye. In this case, either of the DAPI images can be thresholded and then used as a mask. Alternatively, the union of all the pure dye images (preferably individually thresholded) can be used as a mask.

Since the images have been registered, non-zero pixels in each image that fall within the mask can be considered to belong to objects having that dye. Thus, the normalization of the images further includes, for each of the registered pure dye images, determining non-zero pixels falling within the mask (step 115), and normalizing the values of only those non-zero pixels (step 117). The average value of these pixels (or alternatively, the maximum value, the modal value, or even the total integrated intensity of all pixels belonging to objects) can then be used for normalization.

The individual pure dye images, so normalized, are then preferably transformed to ratio images (step 120); if a given pixel position has pixel values $(f_1, f_2, \ldots f_n)$ from the pure dye images, the pixel values in the pure dye images are transformed to $(f_1/\text{sum}, f_2/\text{sum}, \ldots f_n/\text{sum})$, where sum= $f_1+f_2+ \ldots f_n$. Thus each pixel value in a given normalized pure dye image is divided by the sum, taken over all the normalized pure dye images, of the pixel values for that pixel position.

The ratio images are then thresholded, say at 25 or 30% (step 125), and any pixel which is non-zero for a given ratio image can then be considered as having been labeled with the corresponding dye. Note that this approach is much less sensitive to variations in illumination (shading effects) than the first approach of merely thresholding the pure dye images. Each pixel is then colorized (step 130) according to the combinations of dyes considered to have labeled that pixel.

8. Image Digitization

Clearly the pixel values acquired, both for the calibration and for the actual experiment, depend on the digitization parameters (gain, offset, exposure); if one were to use different such parameters, one would obtain images with very different pixel values, and hence, for example, very different color spread matrix, even though the same dye concentrations were present in the scene. These parameters are preferably taken into account in the method.

First of all, note that the above formulation requires that the absence of dye gives zeros for the observed values (i.e., no dye means no signal). Therefore, the first constraint is that the digitizer offset be set just about the clipping point (i.e., at a point where black pixels (i.e., background pixels) have a numerical value just above, just below, or equal to zero). Secondly, for each image acquired, a darkfield correction is required (subtraction of a dark field image, e.g., shutter closed, otherwise acquired under the same conditions). Finally, it may be necessary to also do a background subtraction (local, adaptive algorithm, e.g., top-hat).

As far as exposure time is concerned, it is calibrated (and linear) by definition (i.e., if the pixel value is known for a given exposure time, it can be easily deduced for another exposure time, as long as no saturation occurs); however, with video cameras, changing the exposure time also introduces an offset shift. So, if the exposure time is changed to accommodate changes in signal levels between experiments, or between experiments and the calibration, an accompanying digitizer offset change is preferably made to make background pixels have a gray level of zero or close to zero. Hence another reason to set the offset just about the clipping point, to perform a darkfield correction, and to subtract the local background.

To prevent loss of linearity in the system of linear equations, the digitization parameters are preferably set so that there is no saturation. This saturation is to be avoided both in the CCD (i.e., the exposure is set too high; the well capacity is exceeded) or in the digitizer (i.e., the gain is set too high; the maximum pixel value is exceeded). Therefore, the gain is preferably set at 1 (or very close to 1); larger values would risk saturation, lower values would prevent from detecting CCD saturation. Which specific numerical input corresponds to unity gain will have to be calibrated, system by system (easily done with an oscilloscope, or even better a signal generator).

Another reason for keeping the gain fixed is that, for most digitizers, gain is not calibrated (i.e., it is not known to which gain a given numerical input corresponds), is not very stable, and is not particularly repeatable.

It should be noted here that the above formulation assumed that the exact same image acquisition parameters were used between calibration and actual data acquisition, and therefore that the exact same image acquisition parameters were used to calibrate all dyes with a given filter set (e.g., dye $F_1$ captured with filter set $S_1$ used the same parameters as dye $F_2$ with filter set $S_1$, which are the parameters used for acquiring the raw data with $S_1$; however $F_1$ with $S_2$ could use different parameters). This is obviously too constraining in practice, and indeed does not have to be the case.

It has already been established that the gain is preferably kept fixed at 1 and that the offset is preferably adjusted to operate just at the clipping point. This leaves the exposure time as the last remaining free parameter. As noted earlier, exposure time is calibrated (and linear), so its impact can be accounted for.

If $e_{ij}$ is the exposure time used to calibrate dye j with filter set i, the color spread matrix C can be brought back to the case of unity exposure by dividing each of its coefficients $c_{ij}$ by the corresponding exposure $e_{ij}$. Therefore the result of the calibration is actually the modified color spread matrix $C_1$ (color spread matrix with unity exposure time).

If in the actual experiment, exposure $e_i$ is used to acquire an image with filter set i, Eqs. 1 and 2 above become, respectively $$I = E * C_1 * F \quad \text{[Eq. 7]}$$
$$F = C_1^{-1} * E^{-1} * I \quad \text{[Eq. 8]}$$

where E is a diagonal matrix specifying the exposure time used to acquire each image (i.e., $e_{ij}=0$ if $i \neq j$, $e_{ii}$=exposure time used to capture image with filter set i).

Note that left multiplying by the matrix E is equivalent to multiplying each row of $C_1$ by the corresponding exposure, which is the same as multiplying the right hand side of each of the linear equations by the corresponding exposure. Therefore, in practice, one should left multiply the color spread matrix $C_1$ by the actual exposure times, and then proceed with the SVD.

In conclusion, the digitizer gain is preferably kept fixed at or near 1, the offset is preferably adjusted to operate just at the clipping point, a darkfield correction is preferably applied to each image, local adaptive background subtraction preferably takes place, and the color spread matrix is preferably properly adjusted to account for differences in exposure times.

Note that another approach to the issue of the digitization parameters is to use a digital camera (instead of an analog camera); the gain there is easy to fix at 1 (as a matter of fact, that is all which is offered on some cameras), there is no notion of offset, gray levels are linear with exposure, and darkfielding plus localized background subtraction will take care of the (small) pixel value shifts (dark current etc) which may occur with different exposure times. Also, by providing 10 to 14 bits per pixel, this would improve the precision (and stability) of the subsequent computations (while, in the end, the system might only keep 8 bits of pure dye data, these would be 8 "good" bits). The one disadvantage is that such digital cameras have relatively slow readout rates, hence would give slower frame rates than analog cameras. However, if the light levels were very weak, a choice of a digital, cooled CCD camera might be called for in any case.

9. Practical Considerations

In practice, one obviously tries to choose the dyes and the filter sets so that the matrix C is as close to the identity matrix as possible (and hence so is $C^{-1}$). As a matter of fact, with the currently standard way of acquiring FISH images (monochrome camera; triple band emission filter, triple band polychroic filter, three single band excitation filters; three widely spread dyes, namely blue, green and red), identity of the color spread matrix is precisely the assumption made. Similarly, in [Speicher96], the dyes and epi-fluorescence cubes are chosen such that the color spread matrix is almost diagonal, so that, after thresholding, it can be approximated to the identity matrix. Therefore, the current standard techniques are nothing but simplifications of the color compensation approach.

Also, in practice, one can choose the dyes and filters so that C is well conditioned; and obviously, the closer to diagonal one can make the color spread matrix, the less singular and ill-conditioned it will be.

In the current implementation, using the set of 7 dyes, namely DAPI, FITC, CY3, CY3.5, CY5, Cy5.5, Cy7, the exemplary color spread and color compensation matrices are as follows:

| COLOR SPREAD MATRIX | | | | | | |
|---|---|---|---|---|---|---|
| 0.740000 | 0.000000 | 0.000000 | 0.010000 | 0.000000 | 0.000000 | 0.000000 |
| 0.080000 | 0.840000 | 0.070000 | 0.060000 | 0.020000 | 0.020000 | 0.090000 |
| 0.060000 | 0.150000 | 0.600000 | 0.230000 | 0.050000 | 0.020000 | 0.100000 |
| 0.010000 | 0.010000 | 0.330000 | 0.650000 | 0.040000 | 0.040000 | 0.120000 |
| 0.050000 | 0.000000 | 0.000000 | 0.060000 | 0.680000 | 0.050000 | 0.160000 |
| 0.060000 | 0.000000 | 0.000000 | 0.000000 | 0.210000 | 0.860000 | 0.140000 |
| 0.000000 | 0.000000 | 0.000000 | 0.000000 | 0.000000 | 0.010000 | 0.390000 |

-continued

SINGULAR VALUES

| 1.059813 | 0.913197 | 0.785776 | 0.724402 | 0.617623 | 0.370161 | 0.340714 |

COLOR COMPENSATION MATRIX (INVERSE MATRIX OF COLOR SPREAD MATRIX)

| 1.350690 | −0.002264 | 0.014392 | −0.025687 | 0.000258 | 0.000848 | 0.004326 |
|---|---|---|---|---|---|---|
| −0.118809 | 1.209434 | −0.101343 | −0.072286 | −0.018050 | −0.018838 | −0.216705 |
| −0.113836 | −0.365231 | 2.091644 | −0.695213 | −0.102289 | 0.000416 | −0.196307 |
| 0.048925 | 0.167552 | −1.065018 | 1.900855 | −0.019067 | −0.062710 | −0.320130 |
| −0.098882 | −0.014875 | 0.094547 | −0.168748 | 1.497029 | −0.074572 | −0.556284 |
| −0.070382 | 0.003806 | −0.024192 | 0.043178 | −0.367104 | 1.185891 | −0.283059 |
| 0.001805 | −0.000098 | 0.000621 | −0.001108 | 0.009413 | −0.030407 | 2.571361 |

Another practical consideration is that all computations (SVD calculations, storage of calibrated SVD matrix, SVD matrix multiplication) are preferably carried out at least on 16 bits fixed point integers, and more preferably on single precision floating point pixels.

10. Alternative Filter Configurations

In all of the above discussions, it has been assumed that interference filters (coated glass) were used. However, one could use liquid-crystal tunable filters (LCTF) instead of a multiband emission filter. The main advantage is electronically selectable center wavelength; the main disadvantages are very poor transmission efficiency (10–15%) and high cost ($15 K). Similarly, an alternative for the excitation filter wheel would be an acousto-optics tunable filter (AOTF). The main advantages are very fine bandwidth (1–5 nm), and an average transmission efficiency (40%); the main disadvantages are unavailability of off-the-shelf control electronics and cost. See [Morris94] for a review of both techniques.

Yet another alternative to the excitation filter wheel, is the use of a tunable laser (dye laser), which would provide very narrow bandwidth, electronically switched, at sufficiently high power. However, it is not clear that it could achieve the necessary spectral range (350–750 nm), and the cost would probably be prohibitive.

11. Alternative Generation of Labeled Images

The following discusses how the raw data is processed in order to generate the pseudo-colored, labeled metaphase image.

Instead of solving the set of equations to perform color compensation, one could instead just try matching the spectral signatures to the actually observed values. Each dye, and each combination of dyes, for given filter sets, potentially generates a unique spectral signature (i.e., normalized set of intensities; for the pure dyes, these are the columns of the color spread matrix). The label is then determined on the basis of which of those comes closest to the actual measured data. The first problem is that this requires calibrating not only all pure dyes, but also all combinations; this is a much more cumbersome process (at least 24×7=168 images to acquire). Furthermore, combinations are bound to be much less stable, requiring in effect calibration for each experiment. Finally, even after calibration, this process is also computationally more expensive in order to obtain the processed dye images (for 7 dyes and 24 combinations, there would be at least 336 multiplication and 168 additions per pixel).

Alternatively, again instead of solving the set of linear equations, one could perform cluster analysis on the acquired raw data. The acquired raw pixels, when represented in N-dimensional space (N=number of dyes, counterstain, i.e., DAPI, excluded) should form Q clusters (Q=number of combinations, i.e., 24 or so). By identifying these Q clusters, and assigning all pixels to one of them, it should be possible to directly generate the map of all dye combinations. Rather than operating directly on the raw acquired images, they are preferably first normalized, to eliminate variations in absolute intensities (e.g., normalize with respect to the maximum value; this is similar to what needs to be done when generating the map from the pure dye images).

Cluster analysis is a fairly well covered topic, with available, published, algorithms. The major advantage of this approach, is that it does not require any calibration, and therefore is much less sensitive to experimental variations.

On the other hand, it does not allow one to generate images of is the pure dyes; more critically, one cannot know which cluster corresponds to which dye combination, that is to which chromosome. Another disadvantage is that it involves a rather huge data set (432 K points in 7-dimensional space in the case of 768×576 images with 7 dyes) and hence would probably be computationally very expensive (this could be somewhat improved by eliminating all background pixels).

Another approach which does not require knowledge of the color spread matrix has been described in [Kawata96]. In very broad terms, one works with P×M equations (P=number of pixels, e.g., 430 K, M=number of filter sets, e.g., 7) with P×M+$N^2$ unknowns (N=number of dyes). The unknowns are the pure dye data, plus the coefficients of the color spread matrix. To this one adds P×M+$N^2$ inequalities expressing that the color spread matrix and the pure dye data are non-negative everywhere. Then, using eigenvalue analysis, a solution can be derived [Kawata96]. Advantages are that calibration is not needed, pure dye images can be obtained, and exact identification of dye combinations is possible. However, this obviously involves a rather huge data set, making it computationally cumbersome. This can be helped by eliminating all background pixels; further improvement can be made by considering only a small section of the image at a time.

Yet another approach which does not require knowledge of the color spread matrix is an adaptation of the iterative blind deconvolution method (IBD) described in [Ayers88]. There, the authors were trying to estimate the original data from the knowledge of blurred observed data, without knowledge of the blurring function (point spread function). It is similar to the present problem where it is desired to know the original dye images from the "blurred" observed images without knowledge of the "blurring" function (color spread matrix). This is achieved in a iterative fashion, by making use of the fact that both the dye data and the color spread matrix are non-negative everywhere. Briefly stated, starting from an initial arbitrary estimate of the raw dye data $F_0$ (P×M matrix of the pure dye distributions for all pixels), one can make a first estimate $C_0$ of the color spread matrix by computing $C_0 = I^* F_0^{-1}$ (I=P×M matrix of the observed data for all pixels). $C_0$ is then modified to make all coefficients non-negative, and make all columns sum to 1. Then a new estimate $F_1$ is computed by $F_1 = C_0^{-1}*I$. $F_1$ is then modified to make all values non-negative, conserving the total energy (i.e., spreading the sum of the absolute value of the negative elements of $F_1$ over all positive elements). The loop is then repeated with a new estimate $C_1$ etc. Advantages again are that calibration is not needed, pure dye images can be obtained, and exact identification of dye combinations is possible. However, again, the size of the matrices involved makes it computationally expensive. Here too, one can eliminate all background pixels and/or consider only a small section of the image at a time. In addition, there is no theoretical guarantee of uniqueness of the solution, or even of convergence of the algorithm (even though good results have been obtained in practice).

The above discussion is a reminder that the color compensation method does not absolutely require knowledge of the color spread matrix (and hence calibration); techniques exist which, while mathematically and computationally more complex, do not have this disadvantage.

12. Non-Epi-Illumination Embodiments

A limitation of almost all M-FISH solutions described above is the use of a polychroic mirror. This is actually a limitation not only for the instrument, but also for the wet preparation. Using such a filter limits the choice of dyes which can be used simultaneously; the excitation spectrum of one dye (which corresponds to a reflection band of the polychroic mirror) cannot overlap the emission spectrum of another (which should correspond to a transmission band of the polychroic mirror). It forces one to use less than optimal excitation and emission filters, and therefore results in the very color spreading that requires efforts to undo. Even when dichroic mirrors are used (as in [Speicher96]), the need to use up to 7 of them makes this technique very impractical. One could thus almost say that, from the instrument point of view, the principal culprit for the difficulties of implementation of M-FISH is the poly/dichroic mirror; eliminate it and the solution becomes much easier. Therefore a number of approaches which do not require an epi-fluorescence cube are described here. At present, however, the epi-illumination embodiment described in detail above remains preferred.

Figure 9:
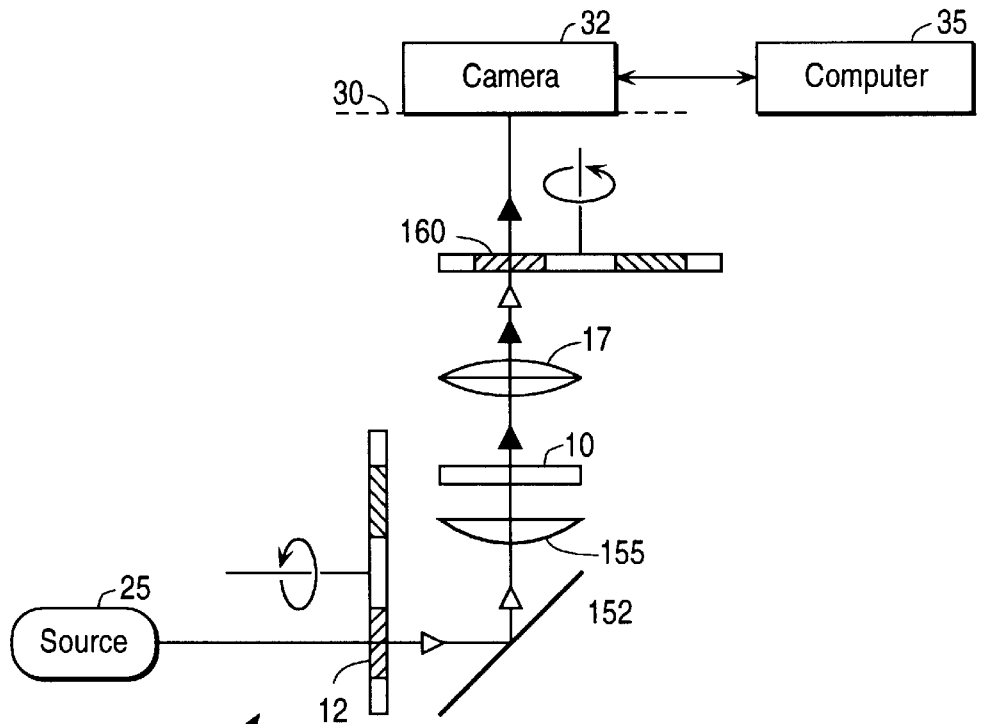
FIG. 9 is a schematic of a representative trans-illumination fluorescence microscope system within which the invention may be embodied.

FIG. 9 is a diagram of a trans-illumination fluorescence (brightfield) microscope system 150. Elements corresponding to those in FIG. 1 are provided with corresponding reference numerals. Excitation radiation from source 25 passes through excitation filter 12 (one of several on an excitation filter wheel), is reflected by a mirror 152 to a condenser 155. The excitation radiation passing through the condenser illuminates sample 10, and proceeds through microscope objective 17 to an emission filter 160 (one of several on an emission filter wheel). The excitation light traveling from the source, through the sample, and to (but not through) the emission filter is shown schematically by hollow arrowheads. Fluorescent radiation emitted from sample 10 passes through objective 17 and through emission filter 20 to form an image in image plane 30. The fluorescent light traveling away from the sample is shown schematically by solid black arrowheads. As in the epi-illumination system, the image is digitized by CCD camera 32 and the digitized image is sent to computer 35 for subsequent processing.

Thus, this embodiment still uses an excitation filter wheel containing single-band excitation filters as in the preferred epi-illumination embodiment. However, the multiple cubes are replaced by the emission filter wheel containing a plurality of N multiband emission filters (i.e., no polychroic mirror is required). Along the lines of the multi-cube embodiment, and according to the present invention, each emission filter is configured for an associated one of N subsets of the total set of dyes, with the $i^{th}$ subset having a plurality of $M_i$ distinct dyes (i ranges from 1 to N). The subsets are chosen so that the $j^{th}$ subset and the $(j+1)^{th}$ subset have one dye in common, referred to as the $j^{th}$ common dye (j ranges from 1 to N−1).

This embodiment has the advantage that all that is required are single-band excitation filters (typically on a filter wheel) and a multiband emission filter wheel (no dichroic or polychroic mirror).

One disadvantage is that the illumination would not be as bright as with epi-illumination (the condenser, which has a lower numerical aperture, is used to focus the light onto the sample, instead of the objective itself); this effect gets worse for high power objectives, as they have higher numerical apertures (as a matter of fact, for low power, low NA objectives, trans-illumination is often brighter than epi-illumination); nevertheless, in the case of M-FISH, the sample should be reasonably bright (whole chromosome paints) and this should not be a major issue.

Furthermore, such an arrangement cannot always fully reject the illumination light (there can easily be $10^6$ excitation photons for each emitted photon); it should be possible to deal with this using holographic notch filters (commonly used to address this problem in Raman spectroscopy, where the problem is much worse). The main advantages are that one can use any dye (even if there is overlap between excitation spectrum of one and emission spectrum of another), any number of them (10 or 12 present no problem with filter wheels, and no particular problem computationally), filter pairs can be optimized independently, etc. It is even conceivable that one could use a single multiband emission filter (instead of a filter wheel), further simplifying the instrument. Epi-illumination is a technique which has worked in the past; recent improvements in the production of interference and holographic filters make it again potentially very useful [Taylor87].

Figure 10:
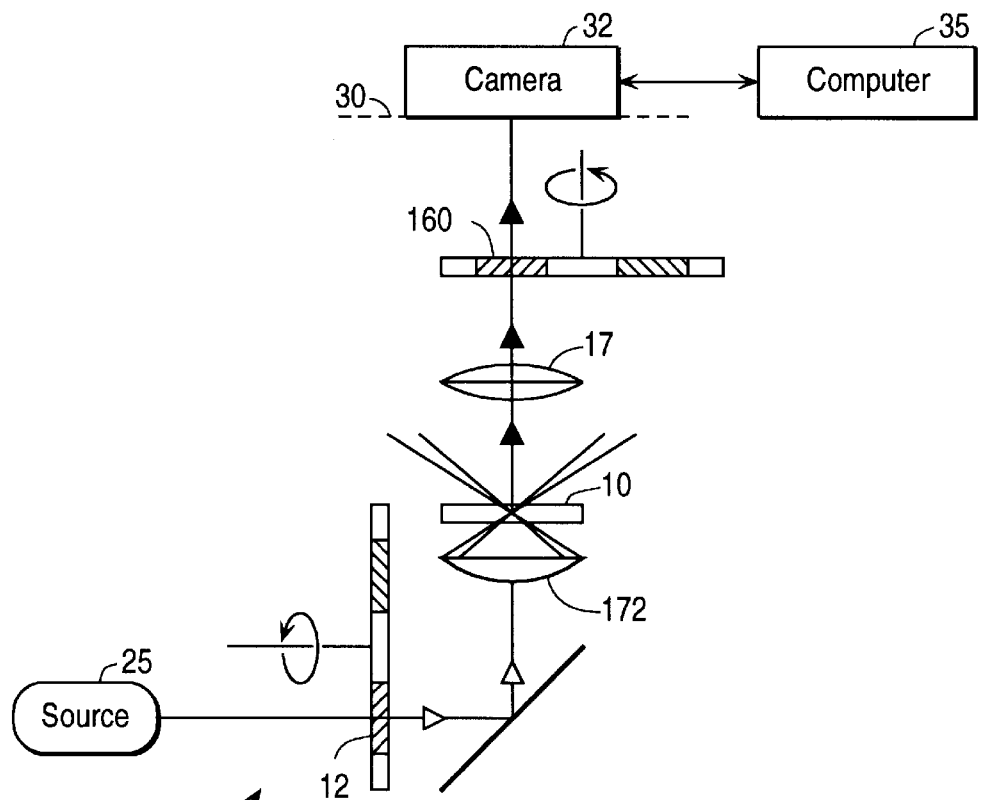
FIG. 10 is a schematic of a representative darkfield fluorescence microscope system within which the invention may be embodied.

FIG. 10 is a diagram of a darkfield fluorescence microscope system 170 that uses a darkfield condenser 172 (available for essentially all microscopes). The conventions of FIGS. 1 and 9 apply. The darkfield condenser produces an annular cone of illumination whose aperture is greater than the aperture of the objective. Therefore, unscattered excitation light does not enter the objective. Here too, the system uses excitation and emission filter wheels, and a darkfield condenser. As in the previously described trans-illumination (brightfield) embodiment, each emission filter is configured for an associated one of N subsets of the total set of dyes, with the $i^{th}$ subset having a plurality of $M_i$ distinct dyes (i ranges from 1 to N). The subsets are chosen so that the $j^{th}$ subset and the $(j+1)^{th}$ subset have one dye in common, referred to as the $j^{th}$ common dye (j ranges from 1 to N−1).

Compared to trans-illumination, this provides much better rejection of the excitation light, but at the cost of reduced brightness (less efficient condenser, reduced NA objective). Advantages over epi-illumination are the same as for trans-illumination [Taylor87].

Yet another approach consists of delivering the excitation light via an optical fiber bundle external to the microscope, and oriented at a very shallow angle with respect to the plane of the sample slide. The excitation light could be delivered either from above or below the slide. Again, an emission filter wheel would be used where each emission filter is configured for an associated one of N subsets of the total set of dyes, with the $i^{th}$ subset having a plurality of $M_i$ distinct dyes (i ranges from 1 to N). The subsets are chosen so that the $j^{th}$ subset and the $(j+1)^{th}$ subset have one dye in common, referred to as the $j^{th}$ common dye (j ranges from 1 to N−1).

If delivery from underneath is practical, then the angle is preferably chosen below the critical angle (total reflection condition), to provide even further rejection of the excitation light (this is the technique described as total internal reflection fluorescence microscopy by some authors [Axelrod87]). Such optical fiber delivery systems are widely available commercially, for a variety of light sources (xenon, mercury, etc); it would probably be required to design a lens to be fitted at the distal end of the fiber bundle, to focus the light on as small a spot as possible. Compared to trans-illumination, this provides much better rejection of the excitation light, while allowing comparable signal brightness. Advantages over epi-illumination are the same as for trans-illumination.

13. References

The following references are incorporated by reference in their entirety for all purposes as if fully set forth herein.

[Axelrod87] D. Axelrod, "Total Internal Reflection Fluorescence Microscopy," in *Fluorescence Microscopy of Living Cells in Culture*, D. L. Taylor, Y. L. Wang eds, Methods in Cell Biology, 30:245–270, Academic Press, 1987.

[Ayers88] J. R. Ayers, J. C. Dainty, "Iterative Blind Deconvolution Method and its Applications," Optics Letters, 13:7:547–549, 1988.

[Bornfleth96] H. Bornfleth, K. Aldinger, M. Hausmann, A. Jauch, C. Cremer, "Comparative Genomic Hybridization Imaging by the One-Chip True-Color CCD Camera Kappa CF 15 MC," Cytometry, 24:1–13, 1996.

[Castleman93] K. R. Castleman, "Color Compensation for Digitized FISH images," Bioimaging, 1:159–165, 1993.

[Castleman94] K. R. Castleman, "Digital Image Color Compensation with Unequal Integration Times," Bioimaging, 2:160–162, 1994.

[Gothot96] A. Gothot, J.-C. Grosdent, and J.-M. Paulus, "A Strategy for Multiple Immunophenotyping by Image Cytometry: Model Studies Using latex Microbeads Labeled with Seven Streptavidin-Bound Fluorochromes," Cytometry 24:214–255 (1996).

[Kawata96] S. Kawata, K. Sasaki, "Multispectral Image Processing for Component Analysis," in *Fluorescence Imaging Spectroscopy and Microscopy*, X. F. Wang, B. Herman eds, J. Wiley & Sons, 1996.

[LeBeau96] M. M. LeBeau, "One FISH, Two FISH, Red FISH, Blue FISH," Nature Genetics, 12:368–375, 1996.

[Morris94] H. R. Morris, C. C. Hoyt, P. J. Treado, "Imaging Spectrometers for Fluorescence and Raman Microscopy: Acousto-Optic and Liquid Crystal Tunable Filters," Applied Spectroscopy, 48:7:857–866, 1994.

[Press92] W. H. Press, S. A. Teukolsky, W. T. Vetterling, B. P. Flannery, *Numerical Recipes in C*, 2nd edition, Cambridge University Press, 1992.

[Speicher96] M. R. Speicher, S. G. Ballard, D. C. Ward, "Karyotyping Human Chromosomes by Combinatorial Multi-Fluor FISH," Nature Genetics, 12:368–375, 1996.

[Taylor87] D. L. Taylor, E. D. Salmon, "Basic Fluorescence Microscopy," in *Fluorescence Microscopy of Living Cells in Culture*, D. L. Taylor, Y. L. Wang eds, Methods in Cell Biology, 29:207–237, Academic Press, 1987.

14. Conclusion

In conclusion, it can be seen that the present invention provides an elegant and cost-effective solution to the image registration problem in M-FISH and related applications.

While the above is a complete description of specific embodiments of the invention, various modifications, alternative constructions, and equivalents may be used, a number of which were described above. Therefore, the above description should not be taken as limiting the scope of the invention as defined by the claims.

What is claimed:

1. In an M-FISH fluorescence system having first and second optical entities for selective insertion into an optical path between a sample and an image plane, the first optical entity having a first multiband transmission characteristic configured to match the emission spectra of a first set of fluorescent dyes, the second optical entity having a second multiband transmission characteristic configured to match the emission spectra of a second set of fluorescent dyes, the improvement wherein:

the first and second sets of dyes have a dye in common so as to facilitate the registration of images made with the first optical entity with images made with the second optical entity.

2. The improvement of claim 1 wherein the system is an epi-fluorescence system.

3. The improvement of claim 1 wherein the first optical entity includes a multiband emission filter and a polychroic mirror.

4. In an M-FISH epi-fluorescence system having first and second polychroic mirrors and first and second multiband emission filters, the first polychroic mirror and the first multiband emission filter being configured to match the excitation and emission spectra of a first set of fluorescent dyes, the second polychroic mirror and the second multiband emission filter being configured to match the excitation and emission spectra of a second set of fluorescent dyes, the improvement wherein:

the first and second sets of dyes have a dye in common so as to facilitate the registration of images made with the first polychroic mirror and the first multiband emission filter with images made with the second polychroic mirror and the second multiband emission filter.

5. A method of analyzing a sample to determine which portions of the sample contain various ones of a set of fluorescent dyes, each dye being characterized by an excitation spectrum and an emission spectrum, the method comprising the steps of:

dividing the set of dyes into first and second subsets having respective first and second pluralities of $M_1$ and $M_2$ distinct dyes;

the subsets of dyes being chosen so that the first and second subsets have one dye in common, referred to the common dye;

providing a first polychroic mirror and a first multiband emission filter, the first polychroic mirror and the first multiband emission filter being configured to match the excitation and emission spectra of the first subset of dyes, and thus referred to as being associated with the first subset of dyes;

providing a second polychroic mirror and a second multiband emission filter, the second polychroic mirror and the second multiband emission filter being configured to match the excitation and emission spectra of the second subset of dyes, and thus referred to as being associated with the second subset of dyes;

for each subset of dyes, generating a plurality of images by directing excitation radiation onto the sample along an optical path that includes that subset's associated polychroic mirror, and directing light emanating from the sample to an image plane along an optical path that includes that subset's associated polychroic mirror and associated emission filter, each of the images in said plurality of images being generated with excitation radiation in a respective one of a plurality of wavelength ranges corresponding to the excitation spectrum of a respective one of the distinct dyes in that subset, and thereby corresponding to a respective one of the distinct dyes in that subset;

correlating (1) an image in the plurality of images generated with the first polychroic mirror that corresponds to the common dye with (2) an image in the plurality of images generated with the second polychroic mirror that corresponds to the common dye to generate a set of registration information;

registering the pluralities of images, so generated, by using the set of registration information, so generated; and using the pluralities of images, so registered, to determine which portions of the sample contain various ones of the set of dyes.

6. The method of claim 5, wherein:

the first polychroic mirror has passbands and reflection bands;

the first emission filter has passbands corresponding to the passbands of the first polychroic mirror; and the plurality of wavelength ranges for the plurality of images corresponding to the first subset of dyes lie in the reflection bands of the first polychroic mirror.

7. The method of claim 5, wherein said step of using comprises, for at least one image that corresponds to a particular dye in a particular subset, correcting measured pixel values in the image for the effect of emissions from other dyes in the particular subset.

8. The method of claim 7, wherein said step of correcting measured pixel values comprises using calibration information developed by generating and analyzing a plurality of images, each image of which is generated with a respective sample having portions containing a respective single dye and substantially no portions containing any other dye.

9. A method of analyzing a sample to determine which portions of the sample contain various ones of a set of fluorescent dyes, each dye being characterized by an excitation spectrum and an emission spectrum, the method comprising the steps of:

dividing the set of dyes into a plurality of N subsets, a given one of the subsets of dyes being denoted the $i^{th}$ subset, where i ranges from 1 to N, with the $i^{th}$ subset having a plurality of $M_i$ distinct dyes;

the subsets of dyes being chosen so that the $i^{th}$ subset and the $(i+1)^{th}$ subset have one dye in common, referred to as the $i^{th}$ common dye;

providing a plurality of N polychroic mirrors, each associated with a respective subset of dyes;

the $i^{th}$ polychroic mirror being configured to match the excitation spectra and emission spectra of the $i^{th}$ subset of dyes;

providing a plurality of N multiband emission filters, each associated with a respective polychroic mirror;

the $i^{th}$ multiband emission filter being configured to match the emission spectra of the $i^{th}$ subset of dyes;

providing a set of single-band excitation filters configured to match the reflection bands of the plurality of polychroic mirrors;

for values of i from 1 to N, generating a plurality of $M_i$ images by directing excitation radiation onto the sample along an optical path that includes a selected one of $M_i$ excitation filters and the $i^{th}$ polychroic mirror, and directing light emanating from the sample to an image plane along an optical path that includes the $i^{th}$ polychroic mirror and the $i^{th}$ emission filter, each of the images in said plurality of $M_i$ images thereby corresponding to a respective one of the $M_i$ distinct dyes;

for values of i from 1 to (N−1), correlating (1) an image in the $i^{th}$ plurality of images that corresponds to the $i^{th}$ common dye with (2) an image in the $(i+1)^{th}$ plurality of images that corresponds to the $i^{th}$ common dye to generate a set of registration information, referred to as the $i^{th}$ registration information;

registering the pluralities of images, so generated, by using the sets of registration information, so generated; and using the pluralities of images, so registered, to determine which portions of the sample contain various ones of the set of fluorescent dyes.

10. The method of claim 9, wherein said step of registering the pluralities of images comprises, for values of i from 1 to (N−1), registering the images in the $(i+1)^{th}$ plurality of images with the images in the plurality of images using the $i^{th}$ registration information.

11. The method of claim 9, wherein said step of using comprises, for at least one image that corresponds to a particular dye in a particular subset, correcting measured pixel values in the image for the effect of emissions from other dyes in the particular subset.

12. The method of claim 11, wherein said step of correcting measured pixel values comprises using calibration information developed by generating and analyzing a plurality of images, each image of which is generated with a respective sample having portions containing a respective single dye and substantially no portions containing any other dye.

13. Apparatus for use with a fluorescence microscope for analyzing a sample to determine which portions of the sample contain various ones of a set of fluorescent dyes, each dye being characterized by an excitation spectrum and an emission spectrum, the apparatus comprising:

a first polychroic mirror and a first multiband emission filter, the first polychroic mirror and the first multiband emission filter being configured to match the excitation and emission spectra of a first subset of dyes, and thus referred to as being associated with the first subset of dyes;

a second polychroic mirror and a second multiband emission filter, the second polychroic mirror and the second multiband emission filter being configured to match the excitation and emission spectra of a second subset of dyes, and thus referred to as being associated with the second subset of dyes;

each subset having a plurality of distinct dyes, the subsets of dyes being chosen so that the subsets have one dye in common, referred to the common dye;

an illumination subsystem for selectively directing excitation radiation in respective ones of a plurality of wavelength ranges corresponding to the excitation spectra of respective ones of the distinct dyes in the set of dyes toward along a first portion of an optical path in the fluorescence microscope; and a mirror support structure for selectively maintaining a desired polychroic mirror and multiband emission filter in a second portion of the optical path.

14. The apparatus of claim 13 wherein the illumination subsystem comprises:

a broadband light source;

a set of single-band excitation filters configured to match the absorption bands of the set of dyes; and an excitation filter support structure for selectively maintaining a desired excitation filter in a first portion of an optical path in the fluorescent microscope.

15. The apparatus of claim 14 wherein the excitation filter support structure comprises a detented rotatable wheel with apertures accommodating the excitation filters.

16. Apparatus for use with a fluorescence microscope for analyzing a sample to determine which portions of the sample contain various ones of a set of fluorescent dyes, each dye being characterized by an excitation spectrum and an emission spectrum, the apparatus comprising:

a plurality of N polychroic mirrors, each associated with a respective one of N subsets of dyes, a given one of the subsets of dyes being denoted the $i^{th}$ subset, where i ranges from 1 to N, with the $i^{th}$ subset having a plurality of $M_i$ distinct dyes;

the subsets of dyes being chosen so that the $i^{th}$ subset and the $(i+1)^{th}$ subset have one dye in common, referred to as the $i^{th}$ common dye;

the $i^{th}$ polychroic mirror being configured to match the excitation spectra and emission spectra of the $i^{th}$ subset of dyes;

a plurality of N multiband emission filters, each associated with a respective polychroic mirror;

the $i^{th}$ multiband emission filter being configured to match the emission spectra of the $i^{th}$ subset of dyes;

a set of single-band excitation filters configured to match the reflection bands of the plurality of polychroic mirrors;

an excitation filter support structure for selectively maintaining a desired excitation filter in a first portion of an optical path in the fluorescent microscope; and a mirror support structure for selectively maintaining a desired polychroic mirror and the associated multiband emission filter in a second portion of the optical path in the fluorescence microscope.

17. The apparatus of claim 16 wherein the excitation filter support structure comprises a detented rotatable wheel with apertures accommodating the excitation filters.

18. The apparatus of claim 16 wherein the mirror support structure comprises a detented rotatable turret.

19. The apparatus of claim 16 wherein the mirror support structure comprises a detented movable slide.

* * * * *